United States Patent [19]

Bucala et al.

[11] Patent Number: 5,700,447
[45] Date of Patent: Dec. 23, 1997

[54] METHODS AND MATERIALS FOR THE DIAGNOSIS AND TREATMENT OF CONDITIONS SUCH AS STROKE

[75] Inventors: Richard J. Bucala, New York; Helen Vlassara; Anthony Cerami, both of Shelter Island, all of N.Y.; Kevin J. Tracey, Old Greenwich, Conn.

[73] Assignee: The Picowder Institute for Medical Research, Manhasset, N.Y.

[21] Appl. No.: 319,747

[22] Filed: Oct. 7, 1994

Related U.S. Application Data

[63] Continuation-in-part of Ser. No. 29,417, Mar. 11, 1993, which is a continuation-in-part of Ser. No. 887,279, May 21, 1992, abandoned.

[51] Int. Cl.$^6$ .................................................... G01N 33/48
[52] U.S. Cl. ............................... 424/9.1; 436/60; 436/71
[58] Field of Search ..................... 424/9.2, 9.1; 435/7.8; 436/60, 71

[56] References Cited

U.S. PATENT DOCUMENTS

| | | |
|---|---|---|
| 4,778,752 | 10/1985 | Curtiss et al. . |
| 4,900,747 | 2/1990 | Vlassara et al. . |
| 4,983,604 | 1/1991 | Ulrich et al. . |
| 5,106,877 | 4/1992 | Ulrich et al. . |
| 5,246,970 | 9/1993 | Williamson et al. . |
| 5,246,971 | 9/1993 | Williamson et al. . |
| 5,273,875 | 12/1993 | Griffith . |
| 5,358,969 | 10/1994 | Williamson et al. . |
| 5,496,735 | 3/1996 | Schwertner ........................ 436/71 |
| 5,561,052 | 10/1996 | Koike .................................. 435/25 |

FOREIGN PATENT DOCUMENTS

| | | |
|---|---|---|
| 0 096439 A3 | 12/1983 | European Pat. Off. . |
| 0 222313 A2 | 4/1987 | European Pat. Off. . |
| WO 85/04169 | 9/1985 | WIPO . |
| WO 93/04086 | 3/1993 | WIPO . |

OTHER PUBLICATIONS

Vlassara et al., "Function of Macrophage Receptor for Nonenzymatically Glycosylated Proteins Is Modulated By Insulin Levels", Diabetes, 35(1), p. 11a (1986).
Vlassara et al., "Accumulation Of Diabetic Rat Peripheral Nerve Myelin By Macrophages Increases With The Presence Of Advanced Glycosylation Endproducts", J. Exp. Med., 160, pp. 197–207 (1984).
Vlassara et al., "Recognition And Uptake Of Human Diabetic Peripheral Nerve Myelin By Macrophages", Diabetes, 34 No.6, pp. 553–557 (1985).
Vlassara et al., "High–Affinity–Receptor–Mediated Uptake And Degradation of Glucose–Modified Proteins: A Potential Mechanism For The Removal Of Senescent Macromolecules", Proc. Natl. Acad. Sci. U.S.A., 82, pp. 5588–5592 (1985).
Vlassara et al., "Novel Macrophage Receptor for Glucose–Modified Proteins is Distinct From Previoiusly Described Scavenger Receptors", J. Exp. Med. 164, pp. 1301–1309 (1986).

Cerami, A. et al., "Role of Nonenzymatic Glycosylation in Atherogenesis", Journal of Cellular Biochemistry, 30, pp. 111–120 (1986).
Radoff, S. et at., "Characterization Of A Solubilized Cell Surface Binding Protein On Macrophages Specific For Proteins Modified Nonenzymatically by Advanced Glycosylation End Products", Arch. Biochem. Biophys., 263 No. 2. pp. 418–423 (1988).
Radoff, S. et al., "Isolation of a Surface Binding Protein Specific For Advanced Glycosylation End Products From The Mouse Macrophage–Derived Cell Line Raw 264.7", Diabetes, 39, pp. 1510–1518 (1990).
Yang, Z. et al., "Two Novel Rat Liver Membrane Proteins That Bind Advanced Glycosylation Endproducts: Relationship to Macrophage Receptor For Glucose–Modified Proteins", J. Exp. Med., 174, pp. 515–524 (1991).
Witztum, J.L., and D. Steinberg, "Role of oxidized low density lipoprotein in atherogenesis", J. Clin. Invest 88, pp. 1785–1792 (1991).
Goldstein, J.L., Y.K. Ho, S.K. Basu, and M.S. Brown, "Binding site on macrophages that mediates uptake and degradation of acetylated low density lipoprotein, producing massive cholesterol deposition", Proc. Nat. Acad. Sci. USA, 76, pp. 333–357 (1979).
Fogelman, A.M. J.S. Schecter, M. Hokom, J.S. Child, and P.A. Edwards, "Malodialdehyde alteration of low density lipoprotein leads to cholesterol accumulation in human monocyte–macrophages", Proc. Natl. Acad. Sci. USA, 77, pp. 2214–2218 (1980).
Sparrow, C.P., S. Parthasarathy, and D. Steinberg, "A macrophage receptor tht recognizes oxidized LDL but not acetylated LDL", J. Biol. Chem., 264 pp. 2599–2604 (1989).
Ross, R. "The pathogenesis of atherosclerosis", An update. New Eng. J. Med., 314, pp. 488–500 (1986).

(List continued on next page.)

*Primary Examiner*—Brian M. Burn
*Attorney, Agent, or Firm*—Klauber & Jackson

[57] ABSTRACT

The in vivo oxidation of lipids and lipid-containing molecules has been discovered to be initiated by the concurrent reaction of such lipid materials with reducing sugars such as glucose, advanced glycosylation endproducts such as AGE-peptides, or a compound which forms advanced glycosylation endproducts, to form materials or particles known as AGE-lipids. AGE-lipids have been implicated in the aging process, the abnormal formation of lipofuscin and in various disease states such as diabetes and atherosclerosis. Diagnostic methods are contemplated, extending in utility from the detection of the onset and course of conditions in which variations in lipid oxidation, AGE-lipid levels, LDL levels, apolipoprotein levels, apolipoprotein receptor binding the like, may be measured, to drug discovery assays. Corresponding methods of treatment and pharmaceutical compositions are disclosed that are based on an active ingredient or ingredients that demonstrates the ability to modulate the levels of all of the foregoing markers of lipid oxidation. A further aspect of the invention relates to the treatment of stroke and related maladies, and to agents and compositions that are prepared for such purpose.

8 Claims, 15 Drawing Sheets

OTHER PUBLICATIONS

Quinn, M.T., S. Pathasarathy, L.G. Fong, and D. Steinberg, "Oxidatively modified low density lipoprotein: a potential role in recruitment and retention of monocyte/macrophages during atherogenesis", Proc. Natl. Sci. USA, 84, pp. 2095–2998 (1987).

Hessler, J.R., D.W. Morel, L.J. Lewis, and G.M. Chisolm, "Lipoprotein oxidation and Lipoprotein–induced cytotoxicity", Arteriosclerosis, 3, pp. 215–222 (1983).

Kugiyama, K., S.A. Kerns, J.D. Morrisett, R.Roberts, and P.D. Henry, "Impairment of endothelium–dependent arterial relaxation by lysolecithin modified low–density lipoproteins", Nature, 344, pp. 160–162 (1990).

Rajavashiesth, T.B., A. Andalibi, M.C. Territo, J.A. Berliner, M. Navab, A.M. Fogelman, and A.J. Lusis, "Induction of endthelial cell expression of granulocyte and macrophage colony–stimulating factors by modified low–density lipoproteins". Nature, 344, pp. 254–257 (1990).

Cushing, S.D., J.A. Berliner, A.J. Valente, M.Navab, F. Parhami, R. Serrity, C.J. Schwartz, and A.M. Fogelman, "Minimally modified low denisty lipoprotein induces monocyte chemotactic protein 1 in human endothelial cells and smooth muscle cells", Proc. Natl. Acad. Sci. USA, 87, pp. 5134–5138 (1990).

Kita, T., Y. Nagano, M. Yokode, K. Ishii, N.Kume, A. Ooshima, H. Yoshida, and A.Kawai, "Probucol prevents the progression of atherosclerosis in Watanabe heritable hyperlipidermic rabbit, an animal mode for familial hypercholesterolemia", Proc. Natl. Acad. Sci. USA, 84, pp.. 5928–5931 (1987).

Esterbauer, H.G. Jürgens, O. Quehenberger, and Koller, E. "Autoxidation of human low density lipoprotein: loss of polyunsaturated fatty acids and vitamin E and generation of aldehydes", J. Lipid Res., 28, pp. 505–509 (1987).

Quehenberger, O., E. Koller, G. Jürgens, and H. Esterbauer, "Investigation of lipid peroxidation in human low density lipoprotein", Free Radical Res. Commun. 3, pp. 233–242 (1987).

Steinbrecher, U.P. "Oxidation of human low density lipoprotein results in derivitization of lysine residues of apolipoprotein B by lipid peroxide decomposition products", J. Biol. Chem., 262, pp. 3603–3608 (1987).

Steinbrecher, U.P., S. Parthasarathy, D.S. Leake, J.L. Witztum, and D. Steinberg, "Modification of low density lipoprotein by endothelial cells involves lipid peroxidation and degradation of low density lipoprotein phospholipids", Proc. Natl. Acad. Sci. USA, 81, pp. 3883–3887 (1984).

Parthasarathy, S., E. Wieland, and D. Steinberg, "A role for endothelial cell lipoxygenase in the oxidative modifications of low density lipoprotein", Proc. Natl. Acad. Sci. USA, 86, pp. 1046–1050 (1989).

Klaassen, C.D. "Heavy metals and heavy metal antagonists", In Goodman and Gilman's The Pharmocological Basis of Therapeutics. A.G. Gilman, L.S. Goodman. T.W. Rall, and F. Murad. Macmillan, New York, pp. 1592–1614 (1985).

Frei, B., Y. Yamamoto, D.Niclas, and B.N. Ames. "Evaluation of an isolumino chemiluminescence assay for the detection of hydroperoxides in human blood plasma", Anal. Biochem., 175, pp. 120–130 (1988).

Frei, B., R. Stocker, and B.N. Ames, "Antioxidant defenses and lipid peroxidation in human blood plasma", Proc. Natl. Acad. Sci. USA, 85, pp. 9748–9752 (1988).

Bucala, R., and A. Cerami, "Advanced glycosylation: chemistry, biology, and implications for diabetes and aging", Adv. Pharmacol. 23, pp. 1–34 (1992).

Njoroge, F.G., and V.M. Monnier, "The chemistry of the Maillard reaction under physiological conditions: A review", Prog. Clin. Biol. Res., 304 pp. 85–107 (1989).

Brownlee, M., A. Cerami, and H. Vlassara, "Advanced glycosylation endproducts in tissue and the biochemical basis of diabetic complications", N.Eng. J. Med., 318, pp. 1315–1321 (1988).

Monnier, V.M., R.R. Kohn, and A. Cerami, "Accelerated age–related browning of human collagen in diabetes mellitus", Proc. Natl. Acad. Sci. USA, 81, pp. 583–587 (1984).

Bucala, R., K.J. Tracey, and A. Cerami, "Advanced glycosylation products quench nitric oxide and mediate defective endothelium–dependent vasodilatation in experimental diabetes", J. Clin. Invest., 87, pp. 432–438 (1991).

Esposito, C., H. Gerlach, J. Brett, D.Stern, and H. Vlassara, "Endothelial receptor–mediated binding of glucose–modified albumin is associated with increased monolayer permeability and modulation of cell surface coagulant properties", J. Exp. Med., 170, pp. 1387–1407 (1989).

Vlassara, H., M.Brownlee, K.R. Manogue, C.A. Dinarello, and A. Pasagian, "Cachectin/TNF and IL–1 induced by glucose–modified proteins: Role in normal tissue remodeling", Science, 240, pp.1546–1548 (1988).

Jain, S.K., R. McVie, J. Duett, and J.J. Herbst, "Erythrocyte membrane lipid peroxidation and glycosylated hemoglobin in diabetes", Diabetes, 38, pp. 1539–1543 (1989).

Nishigaki, I., M. Hagihara, H. Tsunekawa, M. Maseki, and K. Yagi, "Lipid peroxide levels of serum lipoprotein fractions of diabetic patients", Biochem. Med. 25, pp. 373–378 (1981).

Armstrong, D.N. Abdella, A. Salman, N. Miller, E.A. Rahman, and M. Bojancyzk, "Relationship of lipid peroxides to diabetic complications", J. Diabetes Complications, 6, pp. 116–122 (1992).

London, E., and G.W. Feigenson, "A convenient and sensitive fluorescence assay for phospholipid vesicles using diphenylhexatriene", Anal. Biochem. 88, pp. 203–211 (1978).

Jain, S.K., and D. Subrahmanyn, "Two demensional thinlayer chromatography of polar lipids", Ital. J. Biochem. 27, pp. 11–18 (1978).

Havel, R.J., H.A. Eder, and J.H. Bragdon, "Distribution and chemical composition of ultracentrifugally separated lipoproteins in human serum", J. Clin. Invest., 34, pp. 1345–1353 (1955).

Lowry, O., N.J. Rosebrough, A.L. Farr, and R.J. Randall, "Protein measurement with Folin phenol reagent", J. Biol. Chem. 193, pp. 265–275 (1951).

Makita, Z., H. Vlassara, A. Cerami and R. Bucala, "Immunochemical detection of advanced glycosylation end products in vivo", J. Biol. Chem. 267, pp. 5133–5138 (1992).

Makita, Z., H. Vlassara, E. Rayfield, K. Cartwright, E. Friedman, R. Rodby, A. Cerami, and R. Bucala, "Hemoglobin–AGE: A circulating marker of advanced glycosylation", Science, 258, pp. 651–653 (1992).

Kikugawa, K., T. Kojima, S. Yamaki, and H. Kosugi, "Interpretation of the thiobarituric acid reactivity of rat liver and brain homogenates in the presence of ferric ion and ethylenediaminetetraacetic acid", Anal. Biochem., 202, pp. 249–255 (1992).

Ohkawa, H., N. Ohishi, and K. Yagi, "Assay for lipid peroxides in animal tissues by thiobarbituric acid reaction", Anal. Biochem., 95, pp. 351–358 (1979).

Chen, H.-J. C., and A. Cerami, "Mechanism of inhibition of advanced glycosylation by aminoguanidine in vitro", J. Carbohydate Chem. (1996).

Picard, S., S. Parthasarathy, J. Fruebis, and J.L. Witztum, "Aminoguanidine inhibits oxidative modification of low density lipoprotein and the subsequent increase in uptake by macrophage scavenger receptors", Proc. Natl. Acad. Sci. USA, 89, pp. 6876–6880 (1992).

Hicks, M., L. Delbridge, D.K. Yue, and T.S. Reeve, "Catalysis of lipid peroxidation by glucosse and glycosylated collagen", Biochem. Biophys. Res. Commun., 151, pp. 649–655 (1988).

Mullarkey, C.J., D. Edelstein, and M. Brownlee, "Free radical generation by early glycation products: A mechanism for accelerated atherogenesis in diabetes", Biochem. Biophys. Res. Commun., 173, pp. 932–939 (1990).

Pongor, S., P.C. Ulrich, F.A. Bencsath, and A. Cerami, "Aging of proteins: isolation and identification of a fluorescent chromophore from the reactioin of polypeptides with glucose", Proc. Natl. Acad. Sci. USA, 81, pp. 2684–2688 (1984).

Ahmed, M. U., J.A. Dunn, M.D. Walla, S.R. Thorpe, and J.W. Baynes, "Oxidative degradation of glucose adducts to protein", J. Biol. Chem., 263, pp. 8816–8821 (1988).

Grandhee, S.K., and V.M. Monnier, "Mechanism of formation of the Maillard protein cross-link pentosidine. Glucose, fructose, and ascorbate as pentosidine precursors", J. Biol. Chem., 266 pp. 11649–11653 (1991).

Namiki, M., and T. Hayashi, "Formation of novel free radical product in an early stage of Maillard reaction", Prog. Fd. Nutr. Sci., 5, pp.81–91 (1981).

Tsuchida, M., T. Miura, and K. Aibara, "Lipofuscin and lipofuscin–like substances", Chem. Phys. Lipids, 44, pp. 297–325 (1987).

T. Soulis–Liparota, M. Cooper, D. Papazoglou, B. Clarke, and G. Jerums, "Retardation by aminoguanidine of development of albuminuria, mesangial expansion, and tissue fluorescence in streptozotocin–induced diabetic rat", Diabetes, 40, pp. 1328–1334 (1991).

Hammes, H.P., S. Martin, K. Federlin, K. Geisen, and M. Brownlee, "Aminoguanidine treatment inhibits the development of experimental diabetic retinopathy", Proc. Natl. Acad. Sci. USA, 88, pp. 11555–11558 (1991).

Yagishashi, S. M. Kamijo, M. Baba, N. Yagihashi, and K. Nagai, "Effect of aminoguandine on functional and structural abnormalities in peripheral nerve of STZ–induced diabetic rats," Diabetes, 44, pp. 47–52 (1992).

O'Brein, R.C., S. M. Panagiotopoulos, M.E. Cooper, and G. Jerums, "Anti–atherogenic effect of aminoguanidine, an inhibitor of advanced glycation", Diabetes, 41 (Suppl 1) 16A (1992).

Babiy, Alexander V. et al., Biochemical Pharmol., 43(1):995–1001 (1992).

Sakurai, Tamiko et al., Biochemical and Biophysical Research Communications, 177(1):433–439 (1991).

Duell P. Barton, et al., Diabeties, 39:1257–1263 (1990).

Calvo, C. et al., Diabete & Metabolisme (Paris), 14:264–269 (1988).

Ponsin et al., 1991, Diabete & Metabolisme, 17:497–502.

Kirstein et al., 1990, Proc. Natl. Acad. Sci. USA, 87:9010–14.

Pescarmona, 1987, Diabetologia, 30:568A.

Brownlee et al., 1985, Diabetes, 34:938–941.

Corbett et al., 1993, Autoimmunity 15:145–153.

Corbett et al., 1992, Biochemical J. 287:229–235.

Griffiths et al., 1993, Br. J. Pharmacol. 110:963–968.

Williamson et al., 1990, Diabetes and Metabolism 16:369–370.

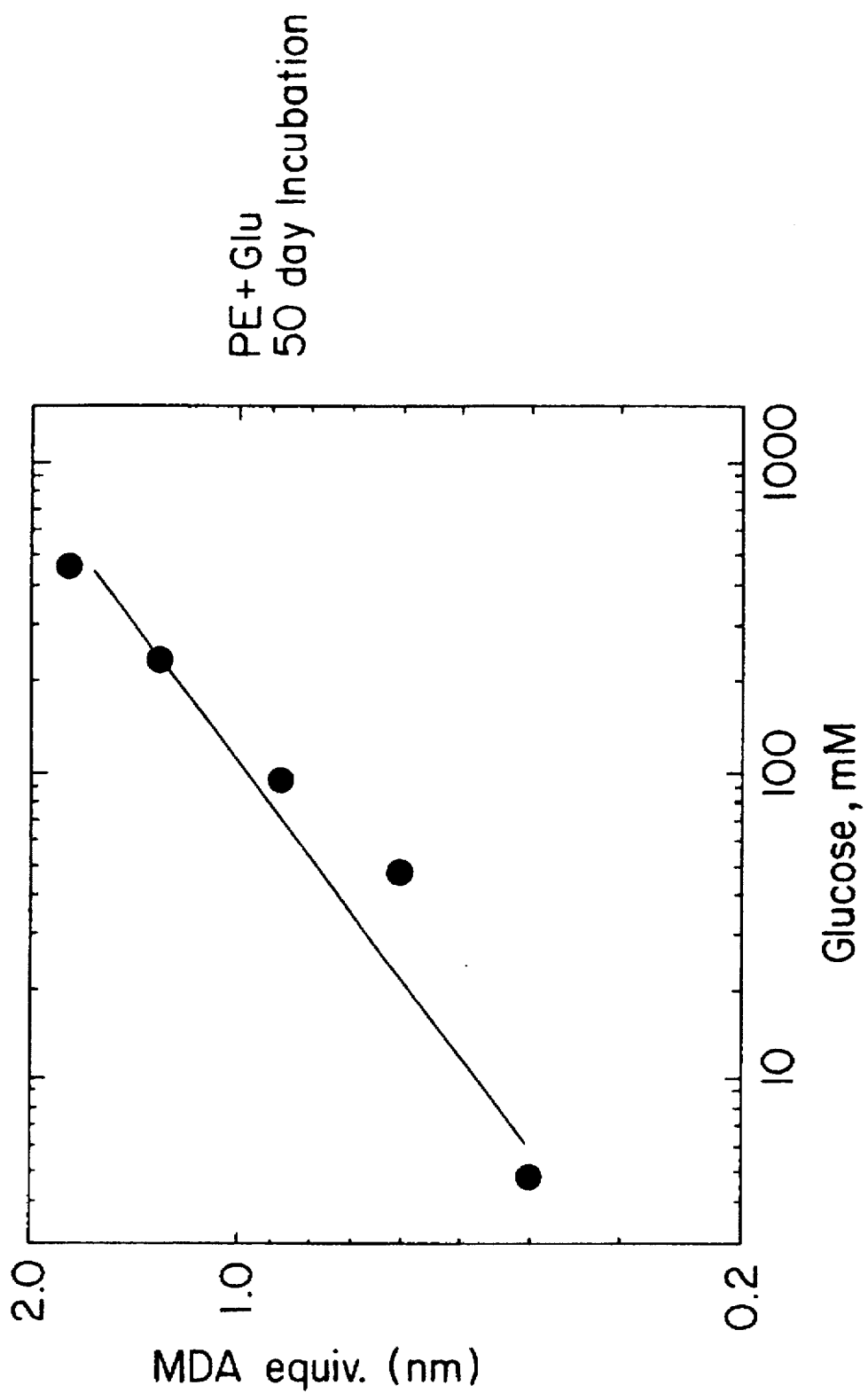

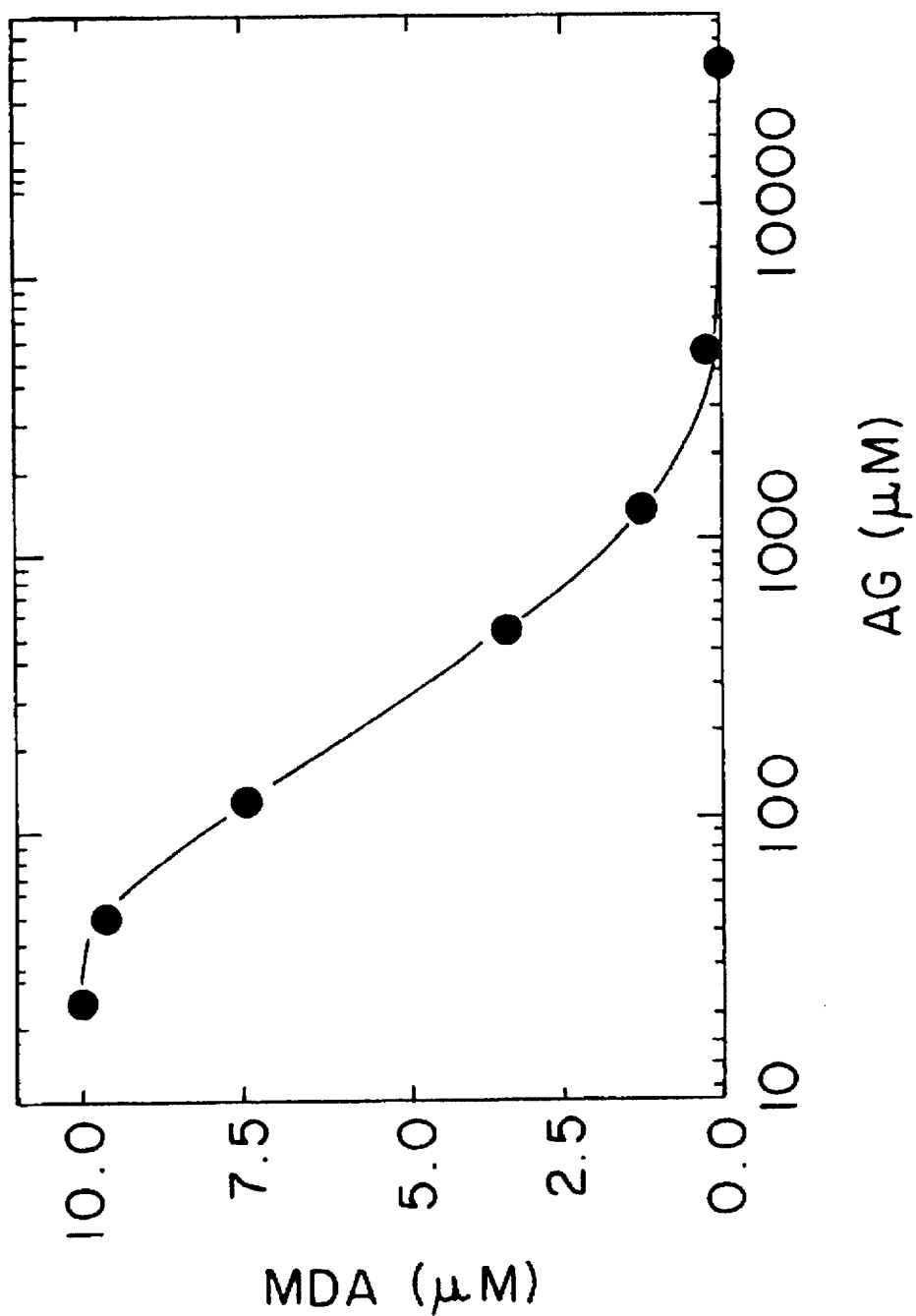

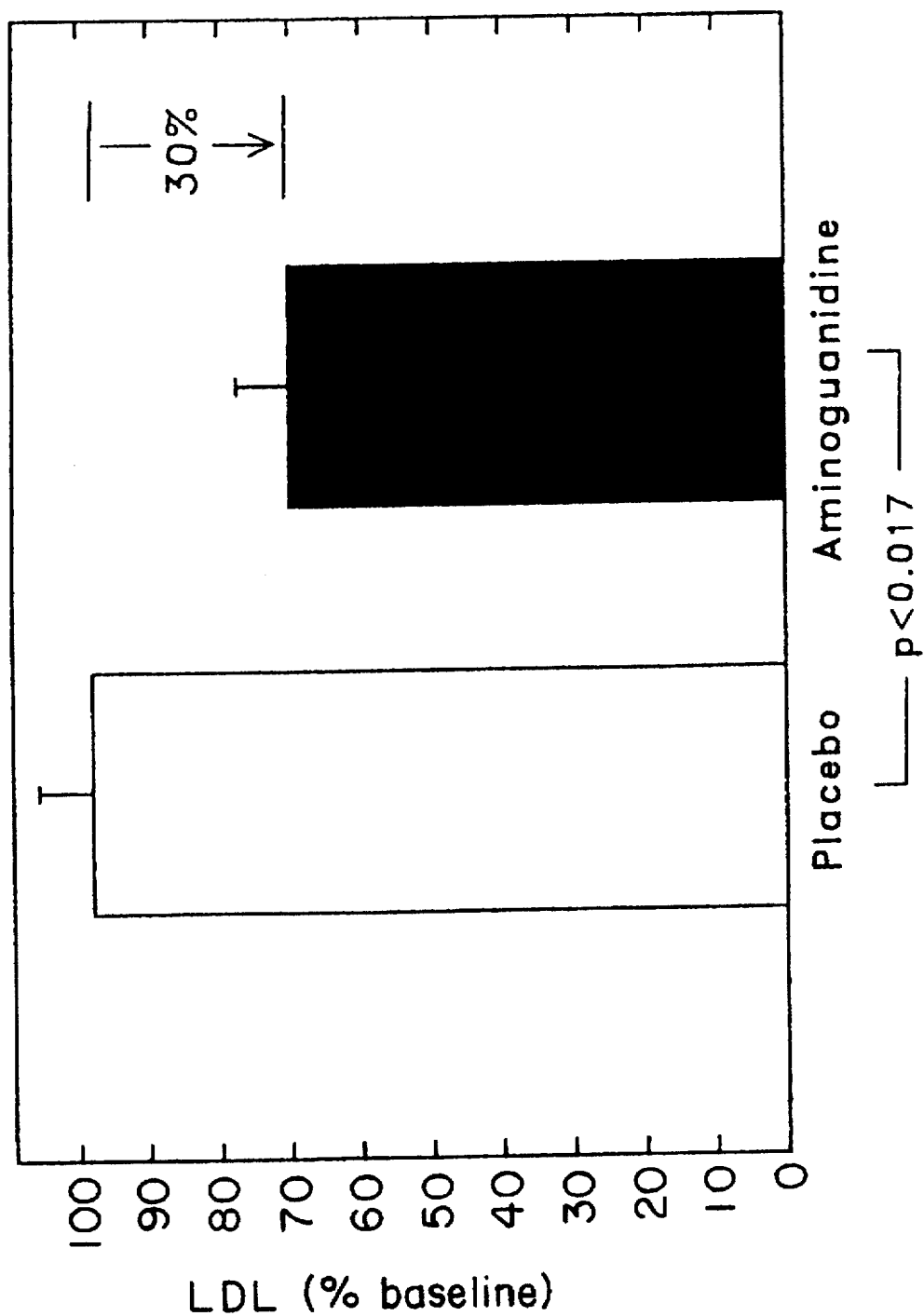

METHODS AND MATERIALS FOR THE DIAGNOSIS AND TREATMENT OF CONDITIONS SUCH AS STROKE

CROSS-REFERENCE TO RELATED APPLICATION

The present application is a Continuation-In-Part of application Ser. No. 08/029,417, filed Mar. 11, 1993 pending, which is, a Continuation-In-Part of application Ser. No. 07/887,279, filed May 21, 1992, now abandoned both by certain of the inventors herein. Priority is claimed under 35 U.S.C. §120 as to the earlier filed applications, and the disclosures thereof are incorporated herein by reference.

This invention was made with partial assistance from grant Nos. AGO-9453, AGO-6943 and DK 19655-15 from the National Institutes of Health. The government may have certain rights in this invention.

RELATED PUBLICATIONS

The Applicants are co-authors of the following articles directed to the subject matter of the present invention: Bucala, R., et al., (1993) "Lipid Advanced Glycosylation: Pathway for Lipid Oxidation In Vivo, P.N.A.S. USA, 90:6434–6438.

TECHNICAL FIELD OF THE INVENTION

The present invention relates generally to the non-enzymatic glycosylation of proteins and other biomolecules and the often consequent formation of advanced glycosylation endproducts (AGEs), and particularly to the formation of lipid-AGEs and the role that glycosylated lipids and lipoproteins may play as markers and actors in conditions such as atherosclerosis and diabetes.

BACKGROUND OF THE INVENTION

Glucose and other reducing sugars attach non-enzymatically to the amino groups of proteins in a concentration-dependent manner. Over time, these initial Amadori adducts undergo further rearrangements, dehydrations and cross-linking with other proteins to accumulate as a family of complex structures which are referred to as Advanced Glycosylation Endproducts (AGEs). Beginning with the early work of the present applicants and extending to the present, substantial progress has been made toward the elucidation of the role and clinical significance of advanced glycosylation endproducts, so that it is now acknowledged that many of the conditions heretofore attributed to the aging process or to the pathological effects of diseases such as diabetes, are attributable at least in part to the formation of AGEs in vivo.

Advanced glycosylation tends to occur on molecules with long half-lives, under conditions of relatively high sugar concentration, such as in diabetes mellitus. Numerous studies have suggested that AGEs play an important role in the structural and functional alteration which occurs during aging and in chronic disease. Additionally, advanced glycosylation endproducts are noted to form more rapidly in diabetic and other diseased tissue than in normal tissue.

A particular area that has received attention in light of the series of discoveries regarding the relationship of advanced glycosylation of proteins to the etiology of conditions such as diabetes and aging, has been the set of events that coincide in the development of vascular disease. Specifically, the formation of atherosclerotic lesions and plaques is an example of a condition that has been extensively investigated with a view to elucidating the interrelationship, if any, that exists between the oxidation of low density lipoproteins (LDL) and the presence and formation of AGEs.

In this connection, research connected with the phenomenon of protein glycosylation has been extended in scope to a broad variety of biological molecules in an effort to first identify the existence of AGE formation in these diverse compartments, and thereafter, to determine the significance, if any, that may be attributable thereto. It is in this context that the discovery of a reaction of this type involving lipids as defined later on herein (eg. the formation of AGE-lipids), was initially presented in parent application Ser. No. 07/887,279, filed May 21, 1992, now abandoned, referred to hereinabove and incorporated herein.

The formation and existence of AGE-lipids was postulated and observed in the said parent application, and the significance of these materials as markers and actors in the conditions already associated with the presence of AGEs, was likewise noted. As stated therein, AGE-lipids are important biologically. The formation of AGEs on lipids has been observed to begin the lipid oxidation process and thus may render these species more active biologically and chemically, and in particular, more prone to deposition on the interior of blood vessels. It is therefore believed that AGE-lipids may be involved to varying degrees in atherosclerosis, stroke and other vascular disease.

For instance, oxidation of the lipid component of low-density lipoprotein (LDL) results in the loss of the recognition of the apo B component by cellular LDL receptors, and in the preferential uptake of oxidized-LDL (ox-LDL) by macrophage "scavenger" receptors. The enhanced endocytosis of ox-LDL by vascular wall macrophages transforms them into lipid-laden foam cells that characterize early atherosclerotic lesions.

The "family" of AGEs includes species which can be isolated and characterized by chemical structure; some being quite stable, while others are unstable or reactive. AGE-lipids may also be stable, unstable or reactive.

When used with reference to endogenous lipids, AGE-lipid compounds are typically formed non-enzymatically in vivo. However, AGE-lipid compounds can also be produced in vitro by, e.g., incubating a mixture of a reducing sugar and a suitable lipid, e.g., a lipid bearing an amino group, or by other methods in vitro, such as chemical coupling of AGEs and AGE models to biological macromolecules.

The reaction between reducing sugars and the reactive groups of lipids may initiate the advanced glycosylation process. This process typically begins with a reversible reaction between the reducing sugar and the reactive group to form a Schiff base, which proceeds to form a covalently-bonded Amadori rearrangement product. Once formed, the Amadori product undergoes further rearrangement to produce the AGE-modified compound.

Although these reactions occur slowly, lipids may accumulate a measurable amount of AGEs in vivo. The resulting AGE-lipids may reduce the structural and/or functional integrity of organs and organ parts, modify the metabolism, or otherwise reduce or impair host function.

As stated in Parent application Ser. No. 07/887,279, (filed May 21, 1992now abandoned) the formation of AGE-lipids is believed to presage atherogenesis and to induce fatty acid oxidation. Correspondingly, it was disclosed that aminoguanidine, an established inhibitor of protein advanced glycosylation also inhibits AGE-lipid formation.

The parent application also disclosed that aminoguanidine reacts directly with malonyl dialdehyde (MDA)-like fatty acid oxidation products, to inhibit the role that they play in continued atherogenesis. This finding was further confirmed in Picard et al. (1992) *Proc. Natl. Acad. Sci. USA*, 89:6876–6880, published in August, 1992, and after the filing date of the said parent application. Picard et al. focused their study on the reaction between MDA and apolipoprotein B (apo B), a protein component of LDL, and performed experiments to determine the ability of aminoguanidine to bind preferentially to MDA to prevent its conjugation to apo B. To establish the environment for these experiments, the authors induced lipid peroxidation by incubation with endothelial cells or with $Cu^{2+}$. The Picard et al. experiments were cumulative with experiments presented earlier by applicants with respect to this specific mechanism of aminoguanidine action, but are limited by the specific in vitro environment chosen, as the physiological oxidation of lipids to form the reactive aldehydes to which aminoguanidine is confirmed to bind in the context of the present invention, will not occur by the means utilized in the article.

More particularly, in vitro studies suggest that the oxidative modification of lipids proceeds via free radical-mediated oxidation of unsaturated bonds that are present within fatty acid residues (12, 13). Polyunsaturated fatty acids are particularly sensitive to oxidation because methylene hydrogens located between paired double bonds are easily abstracted by radical-catalyzed reactions. Diene conjugation occurs and hydroperoxides form. This is followed by fatty acid decomposition, the formation of reactive aldehydes, and in the case of LDL, the covalent modification of apoprotein residues (12, 14, 15).

The biochemical processes that initiate lipid oxidation in vivo remain poorly understood. Triplet oxygen is a poor oxidant under normal, physiological conditions and significant oxidation of LDL in vitro occurs only after the addition of micromolar concentrations of divalent metals such as copper. Lipid oxidation is prevented completely in these incubations by the inclusion of metal chelators such as EDTA (15). LDL oxidation also occurs in diverse cell culture systems and can be inhibited partially by pharmacological blockade of cellular lipoxygenases (16). The precise role of reactive oxygen species in the oxidative modification of lipids in vivo has not been determined, however. Low trace metal concentrations, the high availability of ligands that form tight coordination complexes with metals, and the abundant anti-oxidant capacity of plasma suggest that metal-catalyzed autoxidation and reactive oxygen species play little, if any role in mediating lipid oxidation in vivo (17–19). Further studies confirming the significance of these findings was presented in pending application Ser. No. 08/029,417.

The work discussed above and reviewed later on herein has prompted a further focussed consideration of the etiology of stroke, inasmuch as this condition is frequently the result of atherogenesis. Stroke caused by the abrupt development of cerebral ischemia is the third leading cause of death in the United States. The American Heart Association estimates that there are approximately three million stroke survivors in the United States, most of whom are disabled. Accordingly, the cost of this illness to society in both health care and lost productivity is enormous, by one estimate exceeding 14 billion dollars per annum. Moreover, patients with diabetes mellitus fare less well than non-diabetics with stroke, because they incur more extensive tissue death as compared to non-diabetics after occlusion of a cerebral artery. The extended complications of stroke represent a major problem for diabetics, and adversely influence both quality of life, and morbidity and mortality. The devastating complications of stroke in the diabetic population will assume even greater importance in the coming years, as larger numbers of diabetics survive into their later years when the frequency of stroke increases. Interest in improving the quality of life for these patients has fostered aggressive study aimed at improving treatment. But an incomplete understanding of the pathogenesis of cerebral infarction in diabetics hampers progress in this area, and lends a sense of urgency to identifying responsible factors.

Accordingly, we began to evaluate the hypothesis that diabetes-induced biochemical changes may worsen stroke. It is well known that once a cerebral artery is occluded by a thrombus or embolus, the ultimate size of the resulting infarction is dependent upon a series of pathogenic events occurring in the "ischemic penumbra," the hypoperfused shell of brain that surrounds the densely infarcted zone. Progressive cell neuronal death occurs in the penumbra for hours subsequent to arterial occlusion. Ultimately therefore, factors that modulate neuronal cell death may either attenuate or amplify the size of the resultant stroke.

Early investigators presumed that disruption of a continuous supply of glucose and oxygen to neurons caused cell death by an "energy shortage." But studies by others have suggested that ischemic lesions caused by cerebral arterial occlusion are actually composed of a densely ischemic focus surrounded by a less densely ischemic "penumbral zone". Although the neurons in the dense core are destined to die within minutes, the cells in the penumbra are potentially viable for up to 8 hr. Neuronal death in the penumbra occurs not by rapid energy depletion, but rather by a complex cascade of metabolic and chemical events that mediate neuronal death. This cascade is initially triggered by diminished regional blood flow, but thereafter becomes essentially self- propagating.

A list of the metabolic and biochemical factors implicated in neuronal death in the penumbra includes (but is not limited to) calcium, excitatory neurotransmitters, platelet-activating factor, nitric oxide (EDRF), superoxide radicals, acidosis, transmembrane ion flux, anaerobic glycolysis and cerebral edema. It is now generally accepted that neuronal death in the penumbra is mediated by specific events and factors. This understanding has facilitated development of pharmaceuticals that prevent neuronal death in this critical period. For instance, pharmacological protection against cerebral infarction in the penumbra has been achieved by administering glutamate antagonists that competitively inhibit glutamate binding to the NMDA receptor. Neurons continue to die for an extended period in the penumbra, but targeted therapy administered up to 2 hr after cerebral artery occlusion may confer neuronal protection. Similar success has been achieved with other therapies targeted to events in the penumbra (e.g. calcium channel blockers, PAF antagonists, free radical scavengers, and inhibitors of nitric oxide).

Despite advances in the understanding of stroke pathogenesis, and the identification of the critical role played by cytotoxic events in the penumbra, the pathogenic mechanisms of enhanced cerebral infarction in diabetic patients are unknown. Among the factors that have been proposed (e.g. increased procoagulant activities, micro- and macro-angiopathy, hyperlipidemia, decreased red blood cell deformability, and impaired cerebrovascular autoregulation), perhaps the most widely studied in clinical and experimental investigation is hyperglycemia. Early experimental studies suggested that elevated blood glucose levels during focal cerebral ischemia increase the size of the resulting infarction. These investigators speculated that tissue injury was enhanced by lactate produced from anaerobic glycolysis in the hypoxic penumbra. These experimental observations were supported by clinical studies showing a correlation between glucose levels on admission to the hospital and poor outcome from stroke.

This theory has not received general acceptance however, because elevated glucose levels occur as part of the catabolic stress response to an underlying illness. Thus, higher glucose levels may reflect a more severe stress response to a larger cerebrovascular lesion. Measurements of HbA1c levels in diabetic patients with stroke revealed no correlation with infarct severity, leading other investigators to suggest that the post-stroke hyperglycemia is reactive, derived from the stress response, and does not contribute to increased stroke size. Further complicating the hypothesis, glucose has also been found to confer protection against neuronal death in animal models of focal cerebral ischemia. To date therefore, the role of acutely elevated high glucose levels in the complications of diabetic stroke remains unproven.

To this end, the present inventors have turned to the consideration of the role if any, played by aminoguanidine, a known inhibitor of advanced glycosylation, in infarct size and focal ischemia.

The results presented herein suggest that this agent exerts an effect that may be independent of its known role as an inhibitor of advanced glycosylation.

Accordingly, it is toward the presentation of these findings that the present disclosure is directed.

SUMMARY OF THE INVENTION

In a first aspect of the invention that is the subject of the present application, a method and corresponding compositions are disclosed for the treatment of stroke, which method comprises administering a stroke-ameliorating or stroke-inhibiting amount of an agent capable of averting the occurrence, or beneficially limiting or reducing the size and severity of an ischemic infarct in both diabetic and non-diabetic individuals. More particularly, the method of the invention comprises administering to a patient in need thereof, a therapeutically effective amount of an agent selected from the group consisting of aminoguanidine, α-hydrazinohistidine, analogs of aminoguanidine, and pharmaceutical compositions containing any of the foregoing, all as recited in detail herein. Corresponding pharmaceutical compositions are likewise contemplated, including without limitation, the agents set forth herein as well as additional agents that may then be used in like fashion and for like purpose. This aspect of the invention also contemplates diagnostic procedures and materials including kits, that are useful and effective in the same pathological context.

As the scope of the invention relates in one aspect to the treatment of a condition also recognized as one of the primary sequelae of advanced glycosylation, the present application continues to extend to the subject matter of the parent applications. Accordingly, an important aspect of the invention disclosed and claimed herein continues to be based on the finding that the in vivo oxidation of lipids has been determined to be initiated by the reaction of such lipids to form AGE-lipids as defined herein. Accordingly, the invention extends to a method for modulating the in vivo oxidation of lipids by controlling the formation and presence of AGE-lipids. A corresponding diagnostic utility comprises the measurement of the course and extent of in vivo lipid oxidation by a measurement of the presence and amount of AGEs and particularly, AGE-lipids as defined herein. An assay is included that may use the AGE-lipids of the present invention to identify disease states characterized by the presence of AGE-lipids. Additionally, such an assay can be utilized to monitor therapy and thus adjust a dosage regimen for a given disease state characterized by the presence of AGE-lipids.

More particularly, as the in vivo oxidation of lipids is related to the onset and course of atherosclerosis, the control of in vivo lipid oxidation represents a therapeutic strategy for its treatment, and the invention thus comprises a method for treating atherosclerosis by inhibiting the formation of AGE-lipids. Likewise, the measurement of AGE-lipid levels in mammals represents a method for diagnosing the likelihood or onset of atherosclerosis, or measuring the course or severity of the disease.

As noted above, AGE-lipids are useful as markers of a variety of conditions in which the fluctuation in lipid levels may reflect the presence or onset of dysfunction or pathology. AGE-lipids are also lipid-soluble and are useful alone and in conjunction with known carriers and delivery vehicles, such as liposomes, for the transport of therapeutic and other agents, including in certain instances the AGE moieties themselves, across membranes and epithelial layers, for example, to particular sites in a patient for treatment. The particular site of interest may be one which has at least one AGE receptor which recognizes the AGE-lipid or a portion thereof.

A method of preparing AGE-lipids is also disclosed which comprises incubating the lipid with an advanced glycosylation endproduct or a compound which forms advanced glycosylation endproducts for a length of time sufficient to form said AGE-lipid.

Pharmaceutical compositions are also disclosed that comprise an AGE-lipid in combination with a pharmaceutically acceptable carrier. Such pharmaceutical compositions may include an additional active agent(s) in some instances, and may be prepared and used for oral, parenteral or topical, e.g., transdermal, sublingual, buccal or transmucosal delivery. As stated, the pharmaceutical compositions can be in the form of a liposome in certain instances.

Further, and as set forth in Applicants' parent application, AGE-lipids also demonstrate therapeutic utility and may accordingly be prepared as described above, for administration in controlled quantities to stimulate the uptake and removal of senescent macromolecules, to promote skin rejuvenation or remodeling by such activity, and to serve as a drug delivery means. In this connection, the AGE-lipids and pharmaceutical compositions containing them may be prepared and administered as and where appropriate.

A further embodiment of the invention relates to the concomitant discovery that the in vivo oxidation of LDL is likewise initiated by the formation of LDL advanced glycosylation endproducts (AGE-LDL). AGE-LDL may be formed by reaction with glucose or another in vivo-resident reducing sugar, an advanced glycosylation endproduct, or active fragments thereof, including AGE peptides circulating in the serum of a mammal. More particularly, the formation of AGE-LDL comprises the attachment of AGE moieties to either or both the lipid and apoprotein components, in the latter instance to form AGE-apo B.

Apo B, in turn, has a region within its receptor binding domain that is susceptible to AGE modification. This site may be protected from AGE modification as part of a therapeutic strategy, and may also serve as the focal point of a drug discovery assay or receptor assay in a diagnostic context.

Accordingly, the invention includes a method for diagnosing or monitoring conditions in which serum LDL or cholesterol levels are abnormal comprising measuring the presence and amount of a marker selected from AGE-lipids, AGE-LDL and AGE-apo B. The stated method may be used for example, to diagnose or monitor atherosclerosis and diabetes. A corresponding therapeutic method comprises the treatment of a mammal to modulate, and in the majority of instances, to lower serum LDL or cholesterol levels, by the administration of an agent that serves to modulate AGE-LDL levels, and specifically to inhibit the formation of AGE-LDL.

Also, a method of modulating lipid metabolism in a mammal in need of such treatment is included. The method comprises administering to said mammal a lipid metabolism-modulating effective amount of an agent that can modify the recognition and removal of lipids from serum, and more particularly, such agents as can modify the recognition and binding of apo B by LDL receptors.

Generally, the therapeutic methods of the present invention contemplate the inhibition of in vivo lipid oxidation, LDL level increases or apo B modifications, by the administration of an agent or a pharmaceutical composition containing such agent or a plurality of such agents, for the inhibition of the formation of advanced glycosylation endproducts involving any or all of the lipid and lipid-related materials subject to such in vivo oxidation. Such agents comprise antagonists of advanced glycosylation, and include antibodies to AGEs, antibodies to AGE-lipids, antibodies to AGE-LDL, antibodies to AGE-apo B, as well as other ligands that would bind and neutralize the foregoing antigens. Suitable agents may also be selected from those agents that are reactive with an active carbonyl moiety on an early glycosylation product, and preferably are selected from aminoguanidine, α-hydrazinohistidine, analogs of aminoguanidine, and pharmaceutical compositions containing any of the foregoing, all as recited in detail herein. The inventions set forth herein contemplate the discovery of additional agents that may then be used in like fashion and for like purpose.

In an alternate embodiment and as described in Applicants' parent Application, the in vivo oxidation of lipids, once initiated, is driven by the presence and activity of the lipid peroxidation breakdown products. These include lipid peroxides as well as highly reactive aldehydes such as malonyl dialdehyde (MDA). These aldehydes can react with and/or crosslink to proteins, for example, through available free amino groups. Inhibitors of AGE formation such as aminoguanidine may be used to inhibit the activity of these reactive aldehydes by reacting directly with them. Accordingly, a therapeutic strategy for the treatment of atherosclerosis or other conditions in which LDL levels, cholesterol levels or lipid levels generally, are undesirably high comprises the administration of a therapeutically effective amount of an agent capable of neutralizing the activity of the reactive aldehyde products of in vivo lipid oxidation. Preferred inhibitors include the agents and antagonists recited above, and other materials disclosed herein.

Accordingly, it is a principal object of the present invention to modulate and control the in vivo oxidation of lipids and lipid-like moieties by controlling the formation of advanced glycosylation endproducts (AGEs), and particularly AGEs involving such lipid and lipid-like moieties.

It is a further object of the present invention to provide a method for diagnosing conditions in which abnormal lipid oxidation is a characteristic, by detecting and measuring the presence and extent of lipid-AGE formation.

It is a still further object of the present invention to provide a method for diagnosing and treating atherosclerosis by measuring and inhibiting the formation of AGE-lipids.

It is a still further object of the present invention to provide a method for lowering serum LDL levels, by inhibiting the formation of AGEs including AGE-lipids.

It is a still further object of the present invention to provide a method for identifying new drugs and corresponding agents capable of treating abnormal lipid oxidation, by use of an assay involving AGE-lipids.

It is yet another object is to utilize AGE-lipids to treat certain diseases and conditions, such as skin conditions, or to utilize the AGE-lipid moieties for purposes of delivering disease-treating medications to particular biologically active sites.

It is a still further object of the present invention to identify AGE-lipids and methods of inhibiting the formation in instances or disease conditions where the presence or biological activity of these AGE-lipids is detrimental to the host organism, or indicative of the presence of a disease state in the host organism.

It is likewise a further object of the present invention to provide a method and related compositions for the diagnosis and treatment of stroke and similar maladies, that are based the activity of certain agents that have been identified as AGE inhibitors.

Other objects and advantages will be apparent from a consideration of the ensuing detailed description which proceeds with reference to the following illustrative drawings.

BRIEF DESCRIPTION OF THE DRAWINGS

FIG. 7 is a graph of lipid oxidation changes as a function of glucose concentration;

FIG. 8B is a graph of the inhibition of thiobarbiturate activity as a function of AG concentration.

FIG. 9A compares the AGE modification of LDL apoprotein of non-diabetic and diabetic patients. FIG. 9B compares the AGE modification of LDL lipid of non-diabetic and diabetic patients; and FIG. 9C compares the oxidative modification of LDL of non-diabetic and diabetic patients. Values shown are the mean of duplicate determinations.

FIG. 14 presents histograms depicting the relative lowering of LDL levels (shown as percent of pretreatment baseline) in diabetic patients at the end of a 28-day trial of aminoguanidine versus placebo.

DETAILED DESCRIPTION OF THE INVENTION

Figure 1:
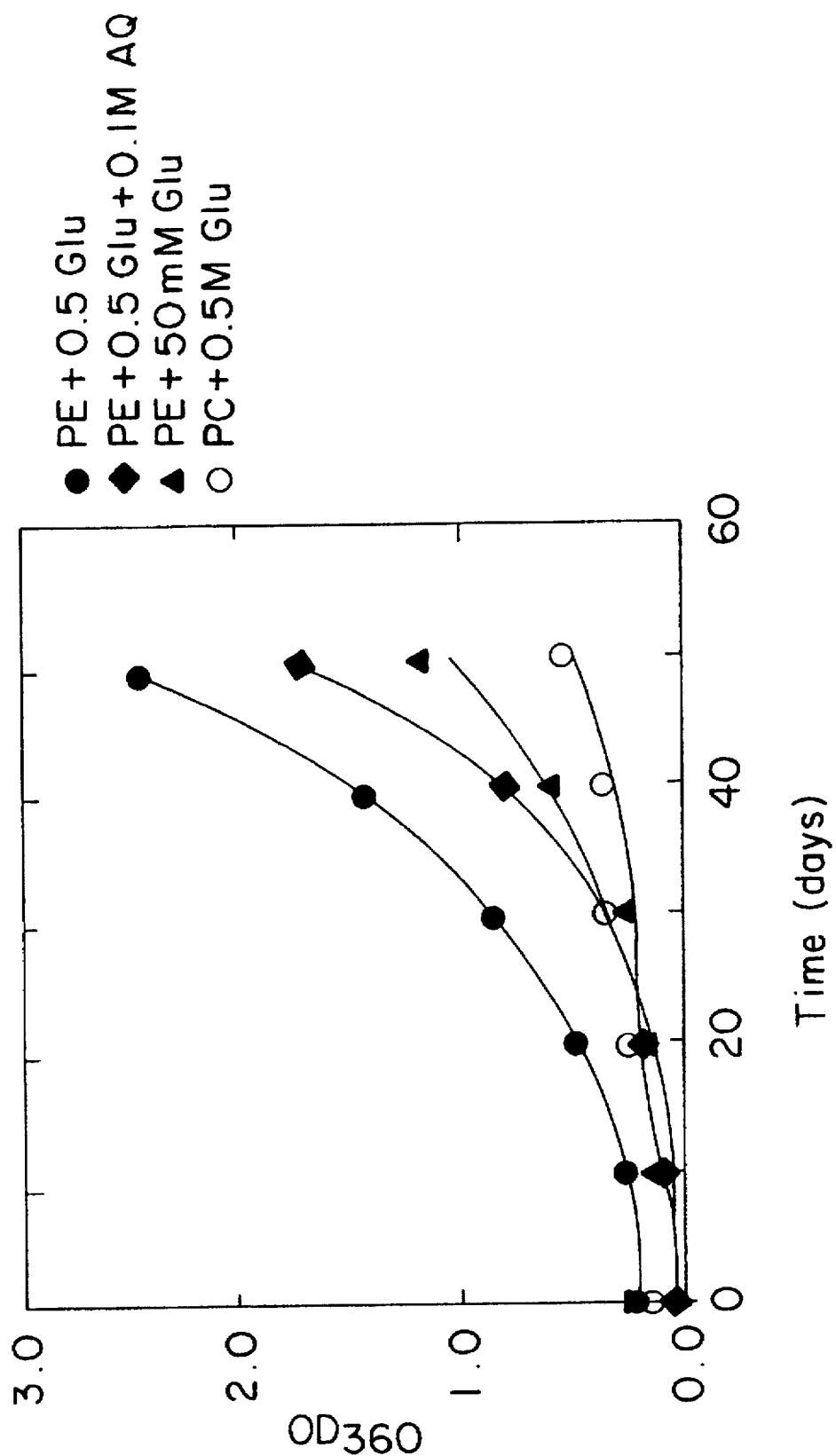
FIG. 1 is a graph of absorbance at 360 nm of AGE-compound formation over time using various lipids incubated with glucose and/or aminoguanidine.

Numerous abbreviations are used herein to simplify the terminology used, and to facilitate a better understanding of the invention. The following abbreviations are representative.

As used herein, the term "AGE-" refers to the compound which it modifies as the reaction product of either an advanced glycosylation endproduct or a compound which forms AGEs and the compound so modified, such as the lipid moiety. AGE-lipids can be formed in vitro by reacting a lipid as defined herein with an AGE, such as AGE-peptide, or either in vitro or in vivo with a compound such as a reducing sugar, e.g., glucose, until the lipid is modified to form the AGE-lipid.

"Lipid" is used in the conventional sense to refer to materials that are soluble to a greater or lesser degree in organic solvents, like alcohols, and relatively insoluble in aqueous media. Thus, the term "lipid" includes compounds of varying chain length, from as short as about 2 carbon atoms to as long as about 28 carbon atoms. Additionally, the compounds may be saturated or unsaturated, and in the form of straight- or branched-chains or in the form of unfused or fused ring structures. Further, these lipid compounds can be optionally linked to other moieties, so long as at least one primary amino group, or other crosslinkable or otherwise reactive group, is present in the molecule.

The term "lipid-related materials" is used herein to encompass not only lipids as conventionally understood and as defined above, but those particles, aggregates and components thereof that are found in connection with lipid moieties. Examples of lipid-related materials included herein include fatty acids, sterol-type molecules, triglycerides, phospholipids, and lipoproteins including apolipoproteins. Preferred lipid-related materials include as the AGE-reactive groups one or more primary amino groups. It is particularly preferred to include at least one primary amino group reactive with AGEs and compounds which form AGEs.

The lipid-related materials that are of primary interest are those that react to form advanced glycosylation endproducts. The resulting AGEs are given herein the common designation of "AGE-lipid(s)" for purpose of convenience and consistency, it being understood that this designation will include within its scope AGEs formed literally with lipid moieties alone, as well as AGEs formed with lipid-related materials such as apolipoproteins. The use of the term "AGE-lipid(s)" in accordance with the present invention is therefore intended to cover such diverse materials within its scope.

Those lipid-related materials that are preferably used in the preparation of the AGE-lipids affirmatively used in the diagnostic and therapeutic methods of the present invention, are phospholipid compounds containing primary amino groups, such as phosphatidylethanolamine. Other lipid-related materials also useful in the present invention are the lipoproteins, particularly those involved in atherogenesis, i.e., low-density lipoproteins (LDLs), and the apolipoproteins that comprise the protein component of LDL, and in particular, apolipoprotein B (apo B).

The AGEs that may be employed to prepare AGE-lipids include such species as 2-(2-furoyl)-4(5)-(2-furanyl)-1H-imidazole ("FFI"); 5-hydroxymethyl-1-alkylpyrrole-2-carbaldehyde ("Pyrraline"); 1-alkyl-2-formyl-3,4-diglycosyl pyrrole ("AFGP"), a non-fluorescent model AGE; carboxymethyllysine; and pentosidine. These compounds have been isolated and characterized as the reaction products which form following the formation of Amadori reactions. However, the in vivo formation of AGEs and the incubation of lipids with AGEs or compounds which form AGEs likely forms AGE species not recited above. Consequently, the invention is not limited to these precise chemical compounds, since other AGE compounds can be formed or have a role in accordance with the teachings herein. Thus, the term AGE can refer to the advanced glycosylation endproduct which the lipid is reacted with as well as the particular form which is produced according to the reaction.

As stated earlier, the present invention is based on the discovery that a relationship exists between lipid oxidation and metabolism, and the in vivo formation of advanced glycosylation endproducts on lipid-related materials as defined hereinabove (AGE-lipids). Particularly, and as supported by the data presented in the parent Application and herein, AGE-lipids appear to initiate lipid oxidation, reduce the efficiency and operation of the body mechanism for LDL clearance by the interruption of normal receptor binding between the apolipoprotein B portion of LDL and appropriate LDL receptors, and leads to increased levels of plasma lipids such as low density lipoproteins (LDL).

This latter observation is believed to reflect the existence of a site for the formation of AGEs that is either adjacent or within the LDL receptor binding domain of apo B. The result of the formation of an AGE on apo B is believed to subject apo B to preferential uptake by macrophage "scavenger" receptors with concomitant inhibition of interaction with the LDL receptor, with the result that the LDL molecules are avidly consumed by the macrophage leading to the formation of undesired foam cells that contribute to atherosclerotic plaque formation. It is therefore of primary interest and importance as a therapeutic strategy, to treat atherosclerosis in more than one way, first by the inhibition of AGE formation and lipid oxidation that, in turn, leads to increased plasma LDL levels, and secondly, to restore the full functionality of apo B uptake by LDL receptors and to avert the formation of undesired foam cells by the consumption of LDL by the macrophage.

A further discovery in accordance with the present invention that forms yet an additional aspect thereof, is the observation that the oxidation of lipids, while initiated by AGE-lipid formation, is further perpetuated by the circulation of certain lipid oxidation byproducts. Also, fatty acid oxidation products such as the malonyl dialdehyde-like compounds participate in protein modification by reaction with free available amino groups. It therefore is desirable as a further therapeutic strategy to neutralize the activity of these oxidation byproducts by a reaction of an appropriate neutralizing agent therewith.

As part of the present invention and as set forth in Applicants' parent disclosure, the inhibitors of advanced glycosylation identified earlier and listed herein in detail, including aminoguanidine, α-hydrazinohistidine, lysine and corresponding analogs, have been found and confirmed to react in such fashion with the MDA-like byproducts and to neutralize the same so that they no longer participate in the modification of proteins. The present invention is not considered to limited or to depend upon a particular mechanism of action, and the foregoing is merely illustrative of the observed beneficial activity of the noted inhibitors.

In view of the above, the present invention includes a dual therapeutic strategy where agents such as aminoguanidine may be administered to inhibit in vivo AGE-lipid formation and consequent initiation of lipid oxidation, and to react with any byproducts of an ongoing lipid oxidation to prevent reaction of these byproducts with proteins as described above.

More particularly, the present invention relates to a method of modulating lipid metabolism including the control and adjustment of such metabolism either to increase or decrease same, by the administration to a mammal or host in need of such treatment, of a lipid metabolism-modulating effective amount of a particular agent or group of agents that are capable of modifying the recognition and removal of lipids from serum, which agents are importantly capable of controlling the formation of AGEs, and particularly AGE-lipids. In selected instances, such as where predetermined quantities of AGE-lipids may act to stimulate the systems of the host to adjust lipid metabolism for therapeutic benefit, the method includes the administration of such AGE-lipids by means described herein in detail.

The lipids subject to advanced glycosylation are as recited earlier, selected from amine-containing lipids, low-density lipoproteins, and apolipoproteins, and particularly in the last mentioned instance, apo B. The method may be practiced to lower low-density lipoprotein levels in a patient, and is applicable for example, to the prevention and/or treatment of hypercholesterolemia, atherosclerosis, and kidney failure.

The agents contemplated for use in this method include materials selected from the group consisting of antibodies against advanced glycosylation endproducts, ligands, including AGE receptors and active fragments thereof, capable of binding to and neutralizing advanced glycosylation endproducts, and compounds capable of inhibiting the formation of advanced glycosylation endproducts. Suitable antibodies include polyclonal antibodies, monoclonal antibodies, chimeric antibodies, and active fragments thereof, all as discussed in detail below. These agents are administered to restore effective lipid metabolism and to correspondingly reduce lipid oxidation. The foregoing appreciates that lipid metabolism is in part controlled by the effective binding of the apolipoprotein apo B to the LDL receptor, so that any compounds or agents contemplated for use in this aspect of the invention, would be capable of interacting with the receptor binding domain of apo B to avert the formation of AGEs adjacent to or therewithin, and to render such receptor binding domain recognizable by the LDL receptor.

As mentioned previously and as supported by one of the examples presented later on herein, it has been observed that such AGE-peptides take an affirmative role in the formation of AGE-lipids and likewise participate in the promotion and acceleration of lipid oxidation and the various consequences thereof. It is therefore desirable, in the instance where such activity is to be inhibited, to neutralize such AGE-peptides by reacting with them to prevent them from promoting further AGE formation. In this connection, aminoguanidine and like inhibitor compounds can be administered.

Concomitant with the above therapeutic strategies are effective diagnostic protocols that may be employed to determine the onset and course of a condition whose measurable variable may include lipid oxidation, by resort to the detection and measurement of the extent of advanced glycosylation of lipids. More particularly, AGE-lipid formation may be detected by means such as the AGE-ELISA developed by the present inventors, to determine the extent of AGE-lipid formation and to thereby assess the extent of lipid oxidation, and consequent effects on plasma LDL levels. Accordingly, measurable increases in lipid oxidation and plasma LDL levels will signal the development and onset of hypercholesterolemia and atherogenesis, so that the present method may be effectively employed to diagnose and monitor the development of vascular disease, and particularly atherosclerosis. Likewise, the presence of AGE-lipids is also reflective of the development and existence of diabetic conditions such as diabetic retinopathy, diabetic and non-diabetic nephropathy, and the like, so that the present diagnostic methods may be used to measure the development and severity of these conditions as well.

With respect to the effect that advanced glycosylation endproduct formation exerts on the ability to clear low density lipoproteins by the recognition and binding of apo B to the LDL receptor, the present invention contemplates and includes the full identification of the receptor binding domain of apo B, and particularly those portions of the receptor binding domain that are presently susceptible to AGE formation. For example, and as set forth later on herein, Applicants have discovered that a particular segment of the receptor binding domain defines lysine with flanking arginine residues, that most likely serves as a site for the formation of the advanced glycosylation endproduct with apo B.

Accordingly, the receptor binding domain may serve as the focal point for a drug discovery assay, where, for example, apo B may be immobilized, and incubated both with agents conducive to the formation of an AGE on the binding domain thereof, and a quantity of a particular drug or inhibitory agent under test. The extent to which the drug serves to either bind with the AGE and thereby inhibit apo B AGE formation, or binds directly with apo B and thereby prevents the same, could then be measured. This particular assay could be prepared as a receptor assay in conjunction with the LDL receptor, to determine whether the apo B receptor binding domain is disabled after incubation with an AGE/AGE-forming materials and a particular drug under test. Both possibilities for drug discovery assays are contemplated herein and are considered within the scope of the present invention.

Both the diagnostic and therapeutic methods of the present invention contemplate the use of agents that have an impact on the formation of AGE-lipids. Among these agents, antibodies to AGEs and other ligands may be prepared and used. These terms are defined below.

The term "antibody" includes any immunoglobulin, including antibodies and fragments thereof that binds a specific epitope, and such general definition is intended to apply herein. The term therefore encompasses polyclonal, monoclonal and chimeric antibodies, the last mentioned described in further detail in U.S. Pat. Nos. 4,816,397 and 4,816,567.

Also, an "antibody combining site" is that structural portion of an antibody molecule comprised of heavy and light chain variable and hypervariable regions that specifically bind antigen. Exemplary antibodies include antibody molecules such as intact immunoglobulin molecules, substantially intact immunoglobulin molecules and those portions of an immunoglobulin molecule that contain the active binding site, including those portions known in the art as Fab, Fab', F(ab')$_2$ and F(v), which portions are preferred for use in therapeutic methods associated herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. (The disclosures of the art cited herein are hereby incorporated by reference.) Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. An antibody may be prepared having a plurality of antibody combining sites, each immunospecific for a different antigen; e.g., a bispecific (chimeric) antibody.

Likewise, the term "ligands" includes such materials as AGE derivatives that would bind to AGE-binding partners, and would include such materials as are prepared by the reaction of AGEs with avidin or biotin, or the preparation of synthetic AGE derivatives that may be prepared from reducing sugars such as glucose, glucose-6-phosphate (G-6-P), fructose and ribose, and peptides, proteins and other biochemicals such as bovine serum albumin (BSA), avidin, biotin derivatives, and enzymes such as alkaline phosphatase. Likewise, enzymes and other carriers that have undergone advanced glycosylation may also serve as ligands in any of the assays of the present invention. Accordingly, carriers such as carbohydrates, proteins, synthetic polypeptides, lipids and biocompatible natural and synthetic resins, and any mixtures of the same may be reacted with sugars to form advanced glycosylation endproducts and may thereby be useful in the present methods. The present diagnostic methods are intended to contemplate all of the foregoing materials within their scope.

The term "AGE binding partners" is intended to extend to anti-AGE antibodies and to other cellular AGE binding proteins or receptors for AGEs, which AGEs may be found on peptides, molecules and cells.

As discussed above, the present invention extends to the preparation and use of AGE-lipids in a variety of diagnostic and therapeutic contexts. With respect to the formation of AGE-lipids, the compounds which form AGEs are typically reducing sugars. Reducing sugars or the AGEs themselves can react with the lipids to form AGE-lipids. However, in in vitro techniques, it is likely that a compound which forms AGEs, such as a reducing sugar, will be used. Examples of reducing sugars include glucose, fructose, ribose and glucose-6-phosphate.

AGE-lipids can be affirmatively used in the treatment, rejuvenation or remodeling of skin. For example, the AGE-lipids can be administered in an amount effective for treating skin ailments or rejuvenating or remodeling the skin, such as to remove or induce the removal of wrinkles. By way of explanation, but not limitation, it is postulated that the application of AGE-lipids to the skin may attract cells, e.g., macrophages, which have the ability to remove naturally occurring AGE-compounds generally from the site of deposition. As a result, in vivo generated and naturally deposited AGE-compounds may be removed and also AGE-lipids and other AGEs may induce cells, e.g., macrophage, T-cells and endothelial cells and fibroblasts, to secrete a variety of substances, e.g., cytokines, growth factors and effector molecules, such as TNF, IL-1, IGF-1, PDGF and other compounds, and collagenase and thereby modulate biological processes, e.g. skin remodeling and wound healing.

The AGE-lipids can be applied to the skin in the form of topical preparations for cosmetic or medicinal use in the form of, e.g., creams, gels or ointments, or can be incorporated into pharmaceutical preparations with other ingredients. Likewise, the topical use of the AGE-lipid compounds described herein could include other agents useful for the treatment of skin ailments or disease, e.g., wrinkling, acne, wound healing etc.

The AGE-lipids of the present invention can also be applied to the skin to modify the effect or use of other medicinal agents. For example, the AGE-lipids could be applied to the skin in conjunction with anti-inflammatory or anti-infective therapeutic agents or other compounds which are effective topically or transdermally. Likewise, such AGE-lipids may enhance the penetration or activity of the other compounds administered in combination.

Additionally, the AGE-lipids may function to attract cells or other endogenous components, e.g., antibodies, which are effective in removing AGEs from the system, or which function in the removal of such compounds from the system. By providing AGE-lipids to the desired site, these cells and other components may be attracted to the area of application and induced to remove other harmful components.

Another aspect of the present invention relates to compositions which can be in any pharmaceutically acceptable form, e.g., transdermal, oral, parenteral, topical (via the skin, inhalation, transmucosally, e.g., rectally, vaginally, buccally or sublingually) as well as other dosage forms administered by other routes of administration. Such compositions typically contain an AGE-lipid which is effective for treating the particular disease or condition, or is effective for attracting, activating or inducing the activity of cells or antibodies to the area of interest in an effort to control, reduce or eliminate the formation of lipofuscin, and other amyloid materials. The amount of the AGE-lipid present in the composition and thus the amount administered will depend upon the particular condition under treatment, as well as the age, weight, and condition of the patient.

Also, the AGE-lipids of the present invention may be useful for the enhancement of the activity of other drugs or therapeutic agents. For example, the AGE-lipid can be coadministered or administered separately from another drug to take advantage of the lipid solubility of the preferred AGE-lipids which are useful herein. Likewise, the drugs can be used essentially simultaneously to attract cells or other biological components, e.g., antibodies, which are to be treated or are necessary or desired in the pharmacological site of activity for purposes of enhancing the activity of the AGE-lipid and/or the other drug.

Another aspect of the invention relates to pharmaceutical dosage forms such as liposomes. Liposomes can be used with AGE-lipids present on the outer layer thereof, or incorporated into the interior, based upon the lipid solubility of the AGE-lipid, the relative size of the liposomes, the presence of other therapeutic agents contained therein, the mode and biological site of intended use/activity and numerous other factors.

Preferred AGE-lipids for use as described herein may take advantage of cellular AGE binding proteins or AGE-receptors as well as the other physical parameters of the AGE-lipids described in the present invention. By way of non-limiting example, the synthetic and naturally occurring AGE, FFI, is recognized by and reactive with macrophage cells (macrophage cells have AGE receptors which recognize FFI) but not particularly reactive with endothelial cells. Thus, if a liposome or other pharmaceutical dosage form containing AGE-lipids is to be delivered such that macrophage cells are targeted, the FFI moiety can be included. In this manner, differences in AGE receptor activity and in the reactivity of different AGEs can be taken advantage of.

Likewise, the AGE-lipids of the present invention can be used to produce antibodies to AGE-lipids, and these antibodies can be used as described herein. For example, antibody formation can be induced by injecting a mammal with an immunogen comprised of an AGE-lipid and then collecting the serum of the mammal. Such serum will typically contain antibodies which recognize and bind to AGE-lipids. These antibodies may be polyclonal or essentially monoclonal, and may be prepared e.g., by using an appropriate immunization protocol, such as a hyperimmunization protocol. Accordingly, appropriate fusion, plating, screening, selection and replication techniques can be utilized to obtain monoclonal antibodies which recognize specific epitopes on the particular AGE-lipid utilized.

The AGE-lipids, antibodies and compositions can also be used in the assessment of the quality, preservation or degradation of stored foods or other biological substances. For example, the presence and concentration of advanced glycosylation endproducts can be identified. This technique is particularly useful in identifying undesirable concentrations of endproducts glycosylation endproducts that accumulate with prolonged storage.

The AGE-lipids, antibodies and compositions can be used in the diagnosis and assessment of certain diseases. For example, the location and concentrations of advanced glycosylation endproducts in the body could be identified. This technique is particularly useful in identifying undesirable concentrations of advanced glycosylation endproducts, such as atheromatous plaques, or for the identification of complications of disease states such as diabetes mellitus.

Of particular diagnostic importance is the identification of AGE-lipids wherein the lipid is a low-density lipoprotein (LDL). In the case of LDL, incubation with glucose or AGE-peptides produces AGE moieties that are linked to both the lipid and to the apoprotein components. Oxidized-LDL forms concurrently with AGEs during these incubations. Aminoguanidine, as well as other known agents for the inhibition of the advanced glycosylation of proteins, inhibits both the advanced glycosylation and oxidative modification processes. Analysis of LDL specimens isolated from the plasma of diabetic individuals reveals increased levels of AGEs on both the apoprotein and lipid components when compared to normal, non-diabetic individuals. The level of LDL oxidation also correlates significantly with AGE modification, indicating that advanced glycosylation may play a primary role in the generation of oxidized lipid in vivo, and that this activity is inhibited by aminoguanidine.

Thus, the identification, by standard assay procedures, of high levels of AGE-LDL in a patient can be utilized to ascertain the precise disease state, as well as to monitor the efficacy of a therapeutic regimen, such as by treatment with an AGE-inhibitor. In a particularly preferred embodiment, the levels of AGE-LDL in a patient can be utilized to diagnose the onset, severity or risk for the development of diabetic conditions and complications in the patient. Additionally, the level of AGE-LDL in a patient can be utilized to diagnose the onset or severity of atherosclerosis and associated conditions in a patient.

The method comprises an assay involving in addition to the analyte, one or more binding partners of AGE-lipids and one or more ligands.

Accordingly, the present assay method broadly comprises the steps of:

A. preparing at least one biological sample suspected of containing said AGE-lipids;

B. preparing at least one corresponding binding partner directed to said sample;

C. placing a detectable label on a material selected from the group consisting of said sample, a ligand to said binding partner and said binding partner;

D. placing the labeled material from Step C in contact with a material selected from the group consisting of the material from Step C that is not labeled; and E. examining the resulting sample for the extent of binding of said labeled material to said unlabeled material.

In a typical non-competitive assay in accordance with the present invention, AGE-lipids are solubilized in methanol and deposited on the assay plate by drying. The assay plates are then hydrated and sequentially exposed to anti-AGE primary antibodies and enzyme-conjugated second antibodies specific for the primary antibodies, with washing steps in between where appropriate. Enzyme levels are then determined by, for instance, substrate conversion protocols well known in the art, and the amount of AGEs can thus be measured by reference to a standard run in parallel.

In a typical competitive assay in accordance with the present invention, an AGE binding protein or AGE receptor may be combined with the analyte and a ligand, and the binding activity of either or both the ligand or the analyte to the receptor may then be measured to determine the extent and presence of the advanced glycosylation endproduct of interest. In this way, the differences in amounts bound between the components of the assay serves to identify the presence and amount of the AGE-lipid.

The present invention also relates to a method for detecting the presence of stimulated, spontaneous, or idiopathic pathological states in mammals, by measuring the corresponding presence of AGE-lipids. More particularly, the activity of AGEs may be followed directly by assay techniques such as those discussed herein, through the use of an appropriately labeled quantity of at least one of the binding partners to AGE-lipids as set forth herein. Alternately, AGEs can be used to raise binding partners or antagonists that could in turn, be labeled and introduced into a medium to test for the presence and amount of AGEs therein, and to thereby assess the state of the host from which the medium was drawn.

Thus, both AGE-lipids and any binding partners thereto that may be prepared, are capable of use in connection with various diagnostic techniques, including immunoassays, such as a radioimmunoassay, using for example, a receptor or other ligand to an AGE that may either be unlabeled or if labeled, then by either radioactive addition, reduction with sodium borotritiide, or radioiodination.

In an immunoassay, a control quantity of a binding partner to AGE-lipids may be prepared and optionally labeled, such as with an enzyme, a compound that fluoresces and/or a radioactive element, and may then be introduced into a tissue or fluid sample of a mammal. After the labeled material or its binding partner(s) has had an opportunity to react with sites within the sample, the resulting mass may be examined by known techniques, which may vary with the nature of the label attached.

The labels most commonly employed for these studies are radioactive elements, enzymes, chemicals which fluoresce when exposed to ultraviolet light, and others.

Suitable examples of radioactive elements include $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. In the instance where a radioactive label, such is prepared with one of the above isotopes is used, known currently available counting procedures may be utilized.

In the instance where the label is an enzyme, detection may be accomplished by any of the presently utilized colorimetric, spectrophotometric, fluorospectrophotometric, thermometric, amperometric or gasometric techniques known in the art. The enzyme may be conjugated to the advanced glycosylation endproducts, their binding partners or carrier molecules by reaction with bridging molecules such as carbodiimides, diisocyanates, glutaraldehyde and the like.

Many enzymes which can be used in these procedures are known and can be utilized. The preferred are peroxidase, β-glucuronidase, β-D-glucosidase, β-D-galactosidase, urease, glucose oxidase plus peroxidase, hexokinase plus GPDase, RNAse, glucose oxidase plus alkaline phosphatase, NAD oxidoreductase plus luciferase, phosphofructokinase plus phosphoenol pyruvate carboxylase, aspartate aminotransferase plus phosphoenol pyruvate decarboxylase, and alkaline phosphatase. U.S. Pat. Nos. 3,654,090; 3,850,752; and 4,016,043 are referred to by way of example for their disclosure of alternative labeling material and methods. A particular enzymatic detecting material is anti-rabbit antibody prepared in goats and conjugated with alkaline phosphatase through an isothiocyanate.

A number of fluorescent materials are known and can be utilized as labels. These include, for example, fluorescein, rhodamine and auramine. A particular fluorescent detecting material is anti-rabbit antibody prepared in goats and conjugated with fluorescein through an isothiocyanate.

The AGE-lipids may be used to produce antibody(ies) to themselves which can be produced and isolated by standard methods including the well known hybridoma techniques. The antibody(ies) can be used in another species as through they were antigen(s) to raise antibody(ies). Both types of antibody(ies) can be used to determine the amount and location of the AGE-lipids in lipid masses, whether in foodstuffs, or in the mammalian body. For convenience, the antibody(ies) to the AGE-lipids will be referred to herein as $Ab_1$ and antibody(ies) raised in another species as $Ab_2$.

The degree of glycosylation in lipid masses suspected of undergoing the same can be ascertained by the usual immunological procedures applicable to such determinations. A number of useful procedures are known. Three such procedures which are especially useful utilize either the AGE-lipid labeled with a detectable label, antibody $Ab_1$ labeled with a detectable label, or antibody $Ab_2$ labeled with a detectable label. The procedures may be summarized by the following equations wherein the asterisk indicates that the particle is labeled, and "Al" stands for the AGE-lipid:

$$Al^* + Ab_1 = Al^*Ab_1 \qquad \text{A.}$$

$$Al + Ab_1^* = AlAb_1^* \qquad \text{B.}$$

$$Al + Ab_1 + Ab_2^* = AlAb_1Ab_2^* \qquad \text{C.}$$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" Procedure, is described in U.S. Pat. Nos. RE 31,006 and 4,016,043. Still other procedures are known such as the "Double antibody", or "DASP" procedure.

In each instance, the AGE-lipid substance forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_1$ may be raised in rabbits and $Ab_2$ may be raised in goats using Ab, as an antigen. $Ab_2$ therefore would be anti-rabbit antibody raised in goats.

Accordingly, a test kit may be prepared for the demonstration of AGE-lipids in a sample, whether in food or in animals, comprising:

(a) a predetermined amount of at least one labeled immunochemically reactive component obtained by the direct or indirect attachment of AGE-lipids or an AGE binding partner to a detectable label;

(b) other reagents; and (c) directions for use of said kit.

More specifically, the diagnostic test kit may comprise:

(a) a known amount of the AGE-lipid (or a binding partner) generally bound to a solid phase to form a immunosorbent, or in the alternative, bound to a suitable tag, or plural such components, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive", "sandwich", "double antibody", etc.), and comprises:

a. a labeled component which has been obtained by coupling a AGE-lipid or a binding partner thereof to a detectable label;

b. one or more additional immunochemical reagents of which at least one reagent is a binding partner or an immobilized binding partner, which binding partner is selected from the group consisting of:

(i) a binding partner capable of binding with the labeled component (a);

(ii) a binding partner capable of binding with a binding partner of the labeled component (a);

(iii) a binding partner capable of binding with at least one of the component(s) to be determined; and (iv) a binding partner capable of binding with at least one of the binding partners of at least one of the component(s) to be determined; and (c) directions for the performance of a protocol for the detection and/or determination of one or more components of an immunochemical reaction between the AGE-lipid and a specific binding partner thereto.

By example, a solid phase assay system or kit may comprise the solid substrate with either bound binding partner and labeled AGE-lipid or bound AGE-lipid and labeled binding partner. A sample to be assayed is then placed in contact with the bound and unbound reagent and a competitive reaction between the labeled material and any unlabeled binding partner(s) in the sample will cause the retention of a dependent quantity of the former on the solid substrate, whereupon it can be precisely quantitatively identified. The foregoing explanation of a particular competitive assay system is presented herein for purposes of illustration only, in fulfillment of the duty to present an enabling disclosure of the invention. It is to be understood that the present invention contemplates a variety of diagnostic protocols within its spirit and scope.

As discussed earlier, the present invention includes potential methods for treating lipids undergoing glycosylation in an effort to retard if not totally inhibit the progress of the Maillard and non-enzymatic glycosylation processes. The method comprises the development of antagonists that when administered to the glycosylating lipid mass, serve by their structure and/or reactivity, to inhibit rather than facilitate the continued glycosylation of the lipid.

For example, the AGE-lipids of this invention can be utilized as adjuvants due to their cross-linking potential with antigens and also as macrophage stimulants to activate the macrophage to effect removal of AGEs. When a lipid-AGE is utilized as an adjuvant it is reacted or cross-linked with an antigen that is "weak". The addition of AGE-lipid to the antigen produces an antigen which produces a strong reaction due to the presence of the AGE-lipid portion, thus increasing the immunogenicity of the original antigen. The invention is not limited to this methodology, but rather encompasses it within its scope.

As noted earlier, phagocytic cells are capable of recognizing and removing abnormal macromolecules by means of receptors on their surfaces which recognize specific chemical structures and bind them. Once the abnormal macromolecule is recognized in this way, the phagocytic cell may internalize the macromolecule and may then degrade it. In some instances, the phagocytic cell may in addition secrete enzymes and other factors to help degrade the molecule or particle extracellularly if it cannot be internalized or to produce other cells to participate in such degradation. After the damaged protein is removed, new growth of normal tissue can ensue, and normal function of the affected area may resume.

Phagocytic cells in the body comprise numerous types of white blood cells. One type of white blood cell, the monocyte, is produced in the bone marrow, and circulates briefly in the blood and thereafter enters the tissues where it becomes a macrophage.

As discussed earlier, the present invention extends to the discovery that the phagocytic cells including monocytes and macrophages can be modified by exposure to stimulator compounds that potentiate the capability of these cells with respect to their recognition and affinity for, and capability to degrade advanced glycosylation end products. In particular, the exposure of these cells to certain stimulator compounds has been found to increase the number of receptors developed on these cells and to thereby increase the capacity and efficiency of these cells with respect to the recognition and degradation of advanced glycosylation endproducts. The AGE-lipids of the present invention can function as stimulator compounds.

Accordingly, the method of the present invention generally comprises exposing the animal body to stimulator AGE-lipids, which cause the body, and its phagocytic cells in particular to become activated and to increase the recognition and removal of target macromolecules that have undergone advanced glycosylation.

Various methods of treatment and use are applicable herein. One preferred use is for the treatment or removal of proteinaceous or fatty deposits such as amyloids or lipofuscin in a mammal. The AGE-lipid, an antibody to AGE-lipids, or a compound which inhibits the formation of AGE-lipids is administered to the mammal in need of such treatment in an amount effective to treat, remove or cause the removal of said lipofuscin.

Another preferred use is for the treatment or prevention of skin disorders, e.g., wrinkling. The AGE-lipid, an antibody to AGE-lipids, or a compound which inhibits the formation of AGE-lipids can be administered to the mammal in an amount effective for the treatment or prevention of wrinkling. All forms of administration are possible, with the most preferred route of administration being topical application in a pharmaceutically acceptable dosage form.

Without limiting the invention to a particular mechanism of action, the AGE-lipid may act directly, having a positive or negative metabolic effect, or indirectly, such as by affecting the activity of, e.g., cytokines or macrophage cells or immunological mediators, for instance, which in turn may cause the desired therapeutic effect.

Also as stated earlier, the invention extends to the discovery that certain compounds that have previously been identified as inhibitors of the advanced glycosylation of proteins, also inhibit the formation of lipid advanced glycosylation endproducts and, further, react directly with malonyl-dialdehyde-like fatty acid oxidation products. These inhibitors of advanced glycosylation endproduct formation in proteins are broadly set forth in U.S. Pat. No. 4,758,583, the disclosure of which is incorporated herein by reference. These compounds include compounds that react with a carbonyl moiety of an early glycosylation product. Representative of such advanced glycosylation inhibitors are aminoguanidine, lysine and α-hydrazinohistidine.

In addition to these specific compounds, other agents capable of inhibiting the advanced glycosylation or proteins have likewise been identified and are also utilizable to similarly inhibit the advanced glycosylation of lipids. These agents are set forth in U.S. Pat. Nos. 4,908,446; 4,983,604; 5,140,048; 5,175,192; 5,114,943; 5,137,916; 5,130,337; 5,100,919; and 5,106,877, the disclosures of which are likewise incorporated herein by reference.

Accordingly, such compounds include a variety of hydrazine derivatives having, for example, a generic formula as follows:

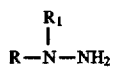

wherein R is a group of the formula

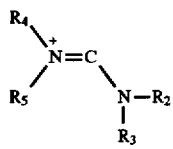

and $R_1$ is hydrogen or a lower alkyl group of 1–6 carbon atoms, a hydroxyethyl group, or together with $R_2$ or $R_4$ may be a lower alkylene bridge of 2–4 carbon atoms; $R_2$ is hydrogen, amino, hydroxy, a lower alkyl group of 1–6 carbon atoms, or together with $R_1$ or $R_3$ is a lower alkylene bridge of 2–4 carbon atoms; $R_2$ may also be an aminoalkylene group of the formula

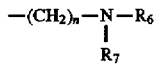

wherein n is an integer of 2–7 and $R_6$ and $R_7$ are independently a lower alkyl group of 1–6 carbon atoms or together form a part of a cycloalkyl or heterocyclic ring containing from 1 to 2 heteroatoms, of which at least one is nitrogen; and the second of said heteroatoms is selected from the group consisting of nitrogen, oxygen, and sulfur; with the proviso that when the second of said heteroatoms of the heterocyclic ring is nitrogen and forms a piperazine ring; it may be optionally substituted by a substituent that is identical to the portion of the compound on the first nitrogen of the piperazine ring; $R_3$ is hydrogen, a lower alkyl group of 1–6 carbon atoms, or together with $R_2$ or $R_4$ is a lower alkylene bridge of 2–4 carbon atoms; $R_4$ is hydrogen, a lower alkyl group of 1–6 carbon atoms or together with $R_1$ or $R_3$ is a lower alkylene bridge of 2–4 carbon atoms; or an amino group; $R_5$ is hydrogen, or a lower alkyl group of 1–6 carbon atoms; with the proviso that at least one of $R_1$, $R_2$, $R_3$, $R_4$ or $R_5$ is other than hydrogen; or R is an acyl or a lower alkylsulfonyl group of up to 10 carbon atoms and $R_1$ is hydrogen; and their pharmaceutically acceptable acid addition salts.

The lower alkyl and lower alkoxy groups referred to herein contain 1–6 carbon atoms and include methyl, methoxy, ethyl, ethoxy, propyl, propoxy, butyl, butoxy, pentyl, pentyloxy, hexyl, hexyloxy and the corresponding branched chain isomers thereof.

The acyl portion referred to herein is a residue of lower alkyl, aryl, and heteroaryl carboxylic acids containing 2–10 carbon atoms. They are typified by acetyl, propionyl, butanoyl, valeryl, hexanoyl and the corresponding higher chain and branched chain analogs thereof. The acyl radicals may also contain one or more double bonds and/or an additional acid functional group, e.g., glutaryl or succinyl.

The heteroaryl groups referred to above encompass aromatic heterocyclic groups containing 3–6 carbon atoms and one or more heteroatoms such as oxygen, nitrogen or sulfur.

The lower alkyl sulfonyl groups of the compounds of this invention are those containing from 1 to 7 carbon atoms and are typified by methylsulfonyl, ethylsulfonyl, n-propylsulfonyl, t-butylsulfonyl and the like.

The term "aryl" as used herein refers to phenyl and lower alkyl substituted phenyl groups containing 6–10 carbon atoms and substituted by one or more substituent groups selected from among chloro, bromo, fluoro, carboxy, lower alkyl, hydroxy, or lower monoalkylamino, lower dialkylamino, and lower alkoxy.

Accordingly, where identified herein, the term "inhibitors of advanced glycosylation" is intended to encompass both the compounds such as aminoguanidine, lysine and α-hydrazinohistidine, and other agents as generically expressed hereinabove and as may be contained in other related patent applications and patents issued subsequently to U.S. Pat. No. 4,983,604 and having reference thereto.

A further aspect of the present invention relates to the role of the above compounds and their analogs in the treatment of stroke and related maladies, such as those involving reperfusion injury or ischemia. As stated earlier and as demonstrated by data presented hereinafter, the relationship of AGEs to the size and severity of ischemic infarct in diabetics prompted an investigation into the role that may be played by aminoguanidine, previously identified as an inhibitor of advanced glycosylation. The experiments that were performed included the administration of aminoguanidine to both diabetics and normals, and the results demonstrate that aminoguanidine exerts a therapeutic effect and beneficially limits or reduces eventual infarct size and severity, unexpectedly even in instances where AGE levels are not abnormally elevated.

In accordance with these findings the present invention extends to the treatment of stroke by the administration of a stroke-ameliorating or stroke-inhibiting amount of an agent capable of at least partially preventing brain damage, or averting the occurrence or reducing the size and severity of an ischemic infarct due, for example, to stroke, aneurism, cerebrovascular accident, apoplexy or other trauma. While not wishing to be bound to a specific theory of action, it is submitted that the activity of aminoguanidine in this instance may proceed in a manner that may or may not relate to the concentration of AGEs in the host or patient. In this context, it is possible and consequently within the scope of the invention that the stroke reducing or inhibiting activity of the present agents may proceed in an AGE- dependent or AGE-independent manner.

The present invention therefore extends to methods for the treatment of stroke and to corresponding pharmaceutical compositions, comprising and including without limitation as active ingredients the inhibitors of advanced glycosylation enumerated herein, such as aminoguanidine, lysine, α-hydrazinohistidine, and the analogs thereof.

In the first group of examples that follow, the effect of AGE-lipids on atherogenesis was demonstrated by the reaction of glucose with the amine-containing lipid, phosphatidylethanolamine (PE). In the presence of EDTA, a nitrogen atmosphere, and at physiological pH and temperature, glucose (5–500 mM) reacts with PE in a time-and concentration-dependent manner to form lipid-soluble products with the spectroscopic properties of AGEs.

AGE formation induced fatty acid oxidation with reaction kinetics that paralleled AGE-associated absorbance and fluorescence. Incubation of glucose with phosphatidylcholine (PC), in which the amine is blocked and unable to react with glucose to initiate AGE formation, resulted in neither spectroscopic changes nor fatty acid oxidation.

Aminoguanidine prevented lipid-AGE formation and lipid oxidation of PE. Again without limiting the invention to a specific reaction mechanism, aminoguanidine may have inhibited fatty acid oxidation by two mechanisms: first, the formation of lipid-associated AGEs was inhibited. Second, the direct reaction with malonyl dialdehyde-like fatty acid oxidation products was inhibited. Lipids containing reactive groups, e.g., primary amino groups therefore react readily with reducing sugars to form AGEs and this induces fatty acid oxidation. Aminoguanidine inhibited the formation of lipid associated AGEs and reacts directly with malonyldialdehyde like fatty acid oxidation products.

In Example 10, the activity of aminoguanidine in the lessening of the effects of stroke is presented and demonstrated. Further details of the above and additional studies are presented below.

EXAMPLE 1

To ascertain whether and to what extent lipids are capable of reacting to form advanced glycosylation endproducts, the lipids phosphatidylethanolamine and phosphatidylcholine were placed into contact with a sugar, preferably a reducing sugar, and allowed to incubate together. Aliquots of the incubation mixture were thereafter assayed as described below, for evidence of the presence of lipid-associated or lipid-attached AGEs. The accumulation of AGEs indicates spontaneous formation of AGE-lipids by non-enzymatically mediated chemical reactions between lipid and sugar precursor compounds.

Methods

Lipid in the form of phosphatidylethanolamine (PE;:L-α-phosphatidylethanolamine, dioleoyl) (1,2-di[(cis)-9-octadecenoyl]-sn-glycero-3-phosphoethanolamine) or phosphatidylcholine (PC) (L-α-phosphatidylcholine, dioleoyl) 1,2-di[(cis)-9-octadecenoyl]-sn-glycero-3-phosphocholine was incubated with glucose (Glu) (L-D-glucose) as follows: Ten mg of PE or PC in $CHCl_3$ solution was evaporated to dryness. To this sample was added 1 ml of glucose (0.5M) in $NaPO_4$ buffer (100 mM, pH 7.4) containing EDTA (1 mM). This solution was previously deaerated by freeze/thawing and saturating the solution with $N_2$ gas. The dried lipid was dispersed in the glucose solution by immersing the sealed tube in a bath sonicator for 30 minutes. Tubes where then placed at 37° C., in the dark, and incubated for the indicated period of time. At intervals, separate tubes continuing parallel incubations (aliquots) were removed, and the lipids extracted for analysis as follows.

Aliquots were shaken with 1 ml of chloroform/methanol (2:1) for ten minutes. After removal of the organic layer, this extraction was repeated twice. The organic layer was then back extracted twice with ice cold, deaerated $H_2O$. After evaporation, lipids were redissolved in chloroform/methanol (1:1) and analyzed by absorption spectroscopy ($OD_{200-800}$ or $OD_{360}$; or fluorescence spectroscopy (excitation wavelength (Ex) 360 nm, emission wavelength (Em) 440 nm).

Figure 2:
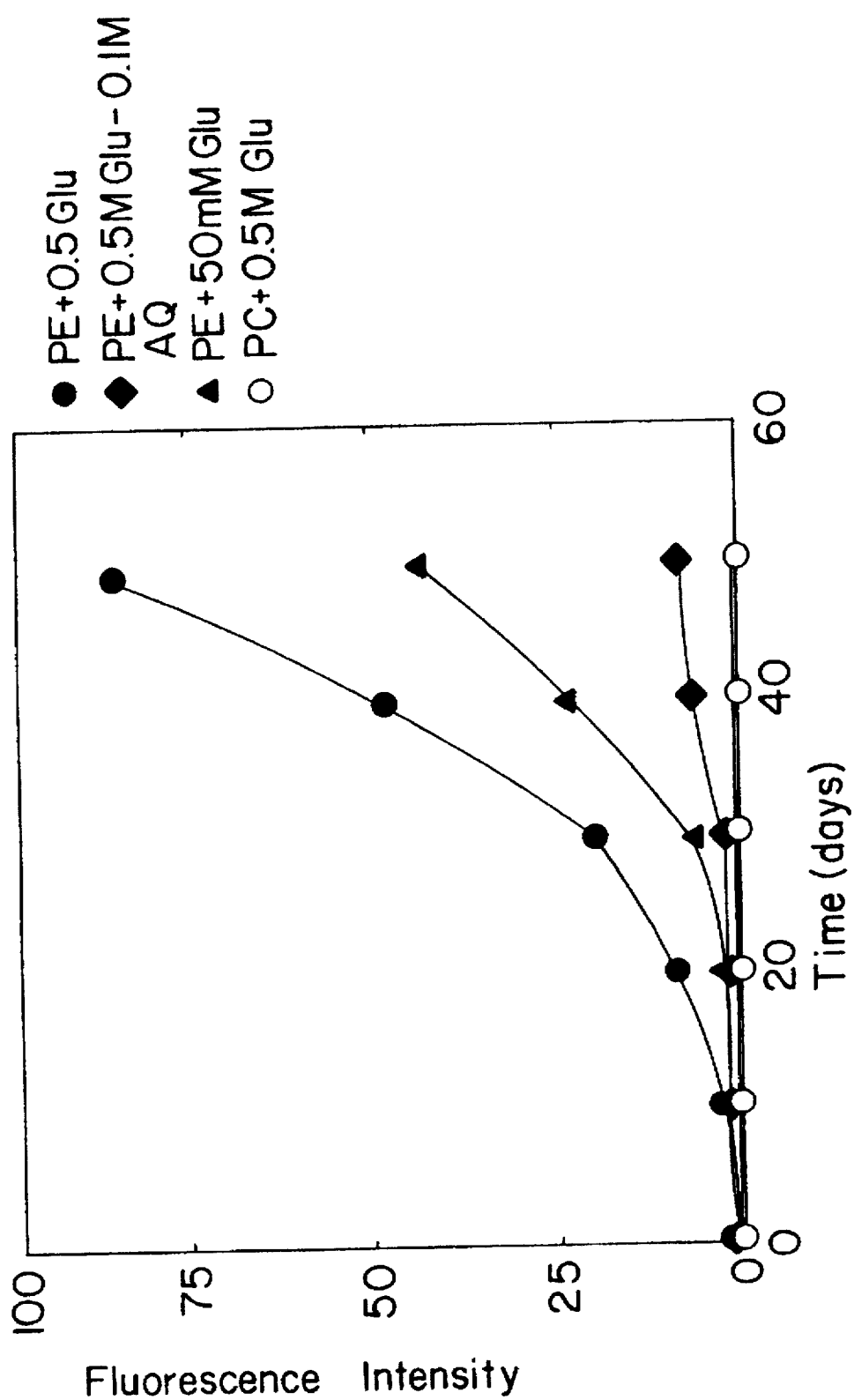
FIG. 2 is a graph of fluorescence intensity using various lipids incubated with glucose and/or aminoguanidine.

The results are shown in FIGS. 1 and 2. FIG. 1 shows the time dependent increase in absorbency at 360 nm, which absorbency is characteristic of AGEs and AGE-containing compounds. As shown FIG. 1, incubation of PE with glucose leads to a significant accumulation of material with AGE-typical absorbance, but incubation of the PC with glucose produces almost none. This result suggests that the free amino group represented in PE may be required for AGE formation while the blocked amino group of PC lacks the reactivity to make AGE formation possible.

FIG. 1 indicates that formation of $OD_{360}$ material depends on glucose concentration; less AGE-specific absorbance is found after incubation of PE with 50 mM glucose than after parallel incubations with 500 mM glucose.

FIG. 1 also indicates that aminoguanidine, an inhibitor of AGE formation on proteins, inhibits AGE-lipid formation as indicated by lower AGE-specific $OD_{360}$ values in incubations for PE with 0.5M glucose and 0.1M aminoguanidine than in parallel incubations of PE and glucose without aminoguanidine.

FIG. 2 shows parallel measurements of fluorescence intensity on the same sets of samples. The results and conclusions are as above. AGE-lipids form spontaneously in incubations of PE and glucose, but not in incubations of PC and glucose. AGE-lipid formation is glucose concentration-dependent, and aminoguanidine inhibits AGE-lipid formation as monitored by the accumulation of AGE-typical fluorescence material.

Figure 4:
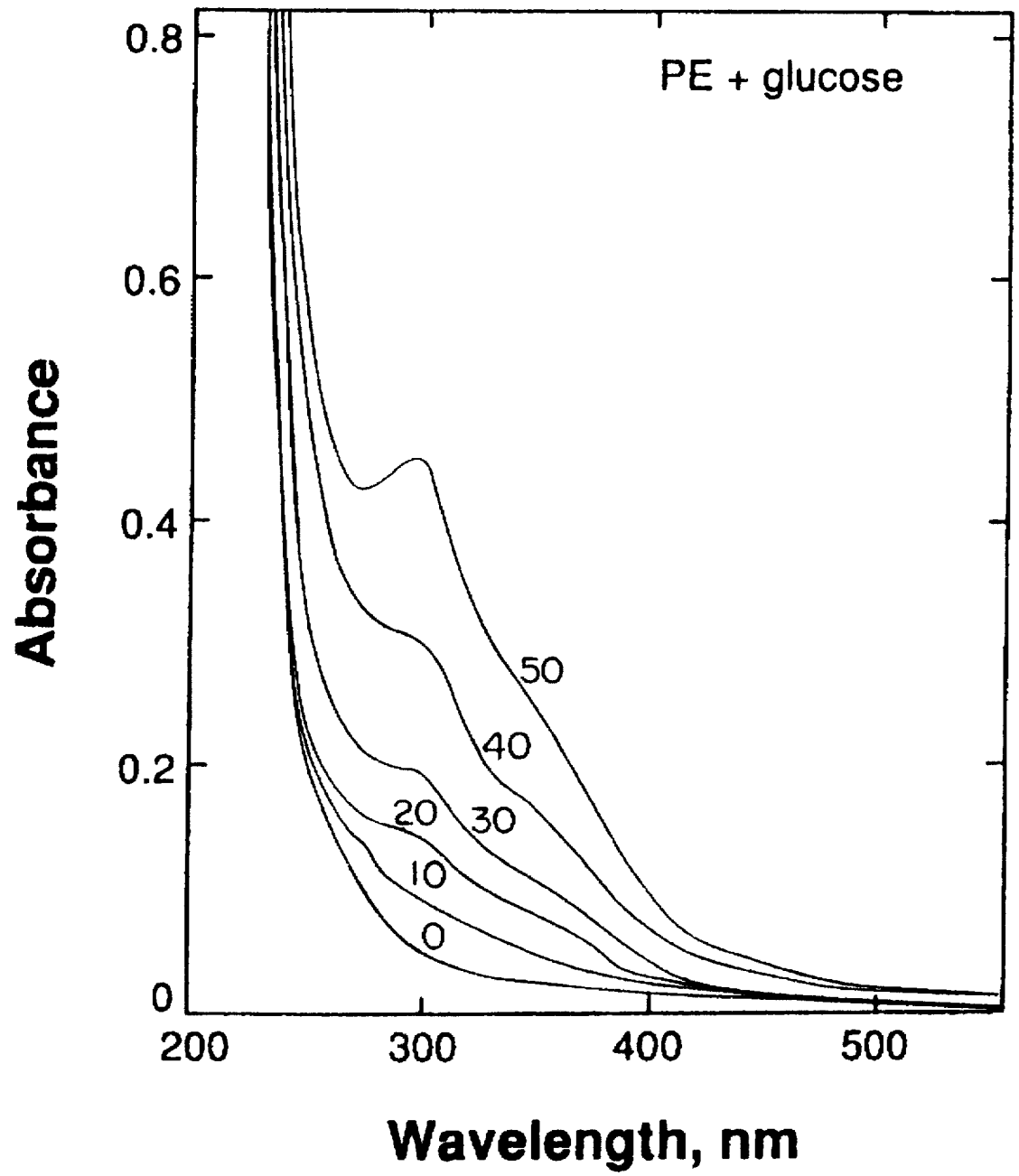
FIG. 4 is a graph of changes in ultraviolet and visible absorbance spectra (200–500 nm) over time (0–50 days) of phosphotidylethanolamine (PE) incubated with 500 mM glucose.

FIG. 4 shows the changes in the ultraviolet and visible absorbance spectrum (200–500 nm) that occur over time when PE is incubated with 0.5M glucose as described above. These changes are characteristic of the formation of AGEs and AGE-like chromophores. FIG. 4 shows that more AGE-typical UV absorbance occurs with progressively longer incubations.

Figure 5:
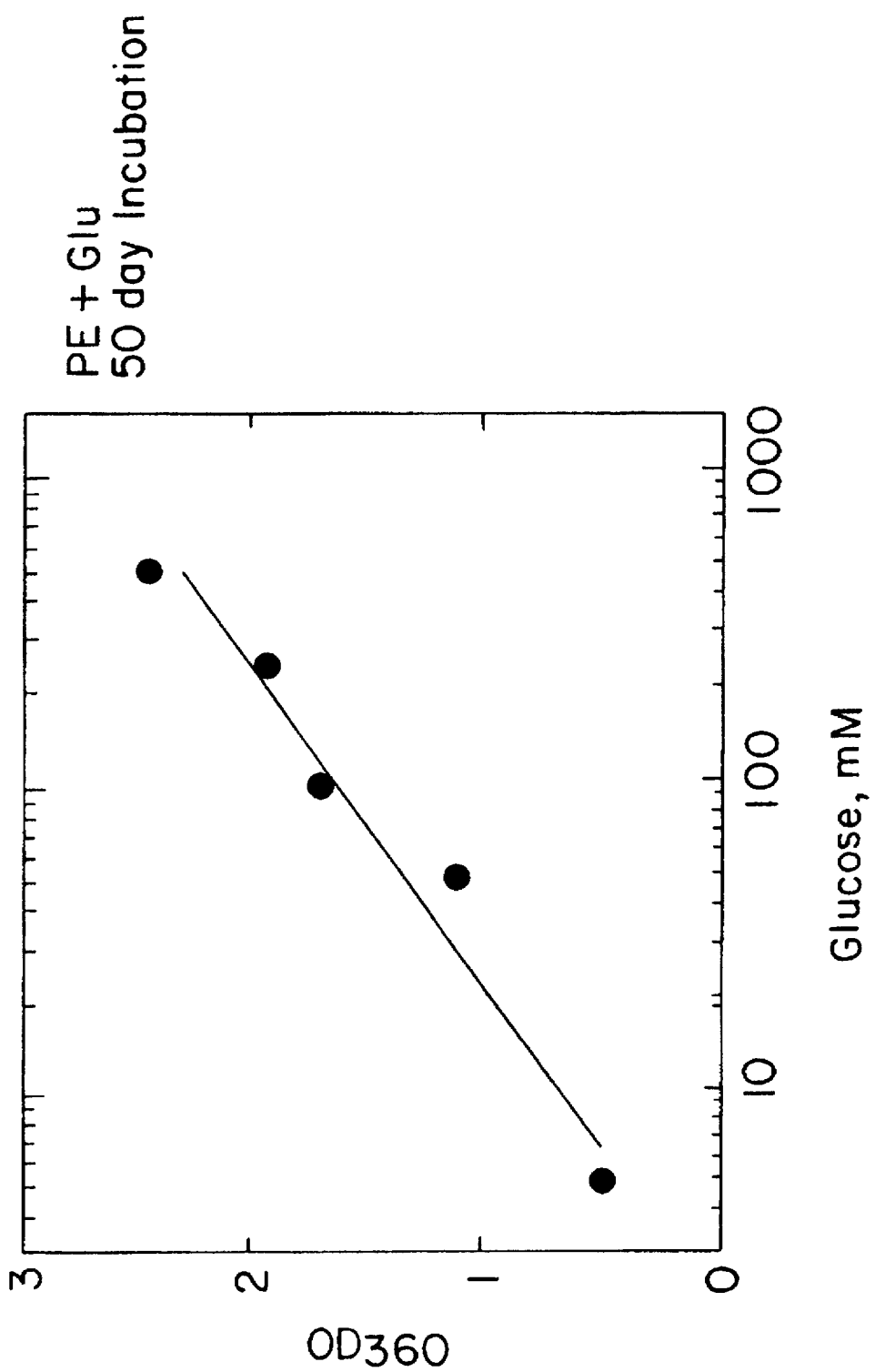
FIG. 5 is a graph of AGE-specific absorbance as a function of glucose concentration.
Figure 6:
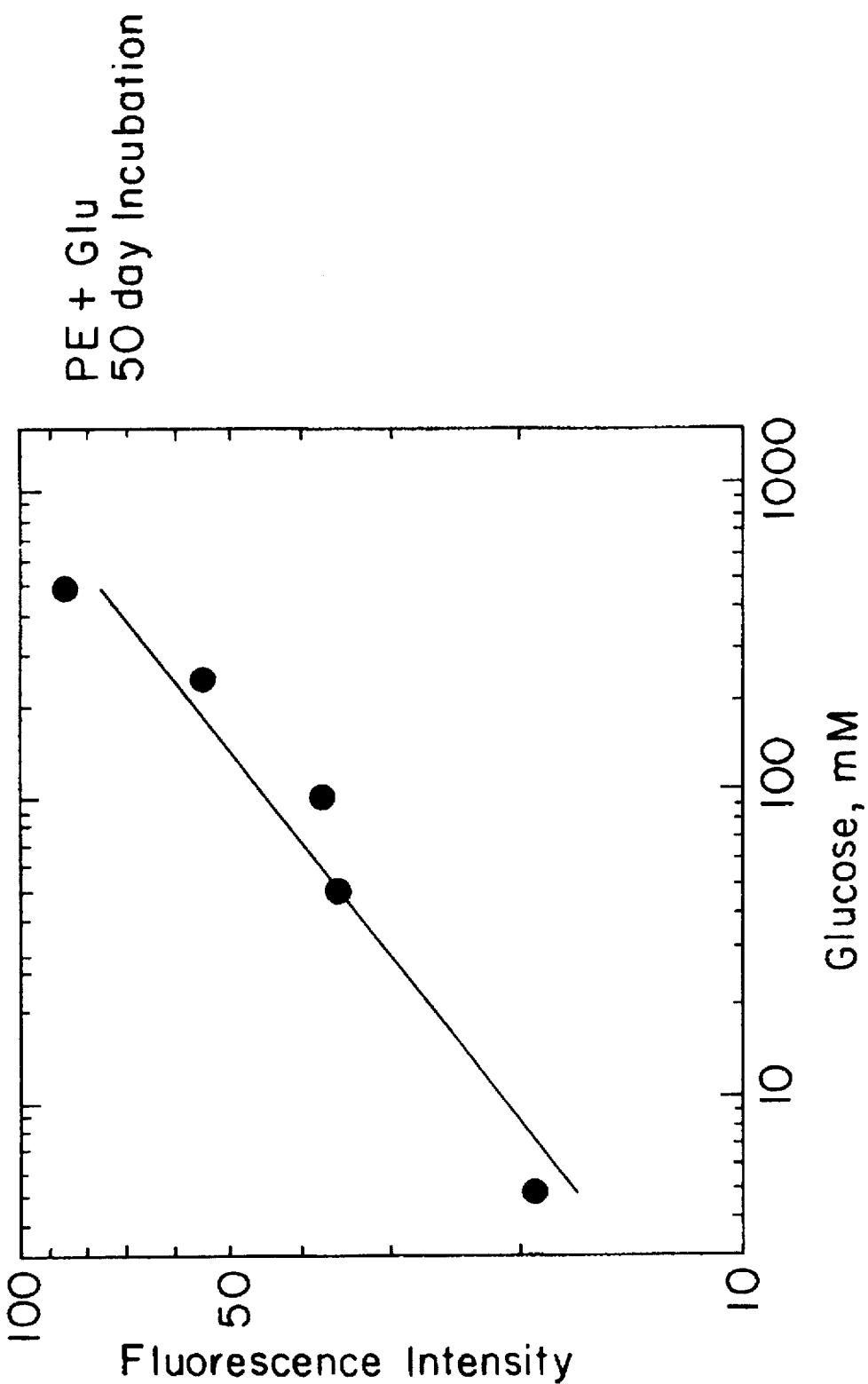
FIG. 6 is a graph of AGE-specific fluorescence as a function of glucose concentration.

FIGS. 5 and 6 show the dependence of AGE-lipid formation on glucose concentration in the incubation mixture. Incubation of PE with glucose for 50 days leads to AGE-specific absorbance (FIG. 5); and fluorescence (FIG. 6). The glucose concentration dependence of lipid oxidation is shown in FIG. 7.

EXAMPLE 2

To demonstrate that AGE-lipid formation is associated with changes in lipid oxidation, the accumulation of malonyldialdehyde (MDA)-like oxidation products was measured in samples from the incubations described above.

Methods

Lipid peroxidation products were quantified by the thiobarbituric acid reactive substances methods (TBARS; PROC. NATL. ACAD. SCI. USA 81:3883–3887). Briefly, 0.1 ml of lipid extract was added to 0.2 ml of TBA reagent (0.37% thiobarbituric acid, 10% trichloroacetic acid) and heated to 100° C. for 30 minutes. n-Butanol extractable material (1 ml) was then analyzed by fluorescence spectroscopy (emission at 553 nm upon excitation at 515 nm). Thiobarbituric acid-reactive substances were quantitated by comparison of duplicate experimental samples to an MDA standard curve that was obtained by assaying in duplicate, 0.1–20 nmole of MDA. Oxidative modification values are expressed as MDA equivalents (pmMDA(eq)/μg lipid).

Results

Figure 3:
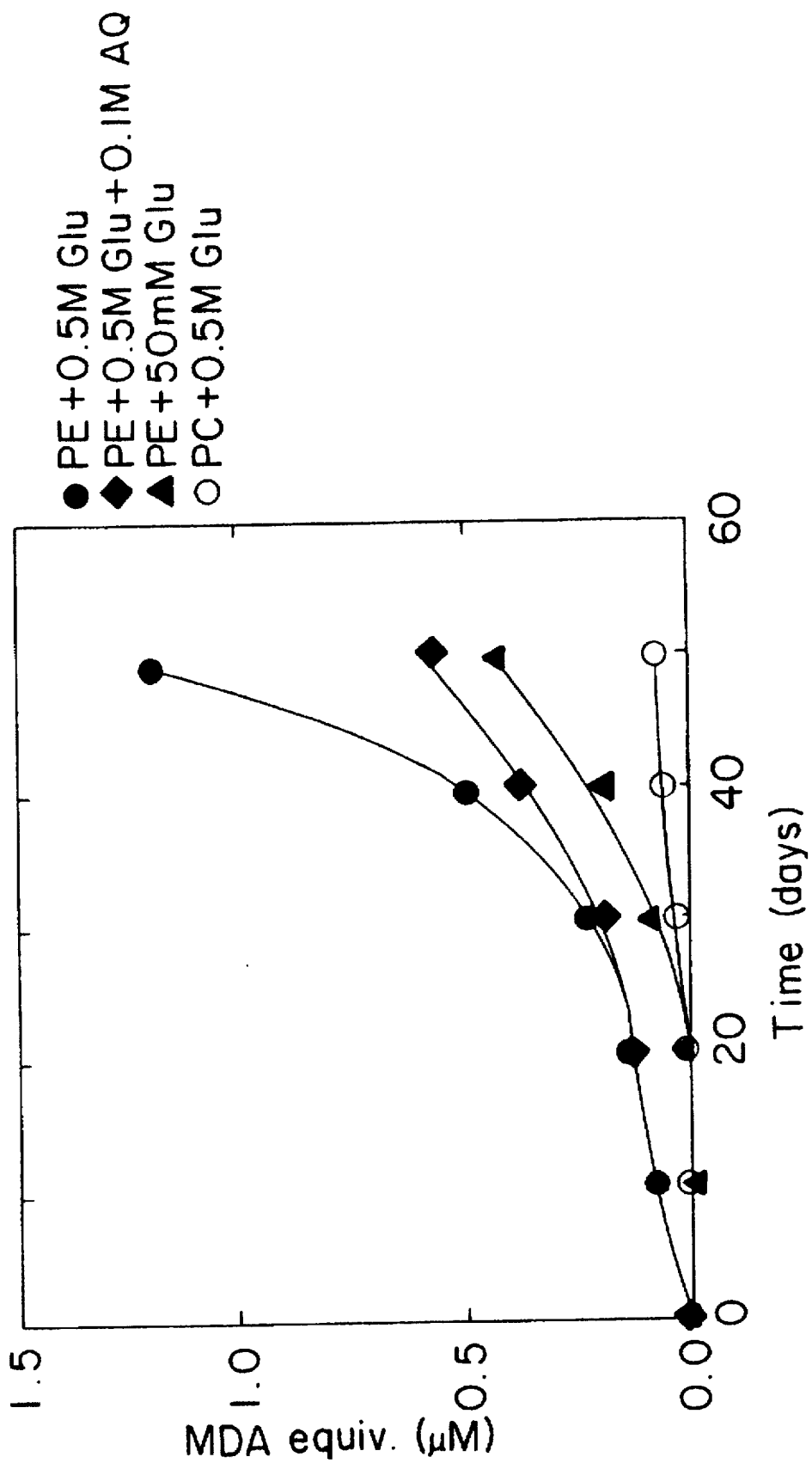
FIG. 3 is a graph of lipid oxidation in relation to AGE-lipid formation using various lipids incubated with glucose and/or aminoguanidine.

FIGS. 3 and 7 show that lipid oxidation increased in conjunction with AGE-lipid formation. Specifically, incubation of PE with glucose led to lipid oxidation in a time- (FIG. 3) and glucose concentration- (FIG. 7) dependent fashion. Incubations of PC with glucose led to little or no lipid oxidation (FIG. 3), and aminoguanidine inhibited oxidation of lipid in PE/glucose incubations (FIG. 3).

EXAMPLE 3

The formation of AGEs on lipids was additionally assessed by AGE-specific ELISA.

Methods

Lipids (PE or PC) were incubated with glucose as described above. AGE content was quantitated by ELISA using a specific anti-AGE antibody (see Makita et al., *J. BIOL. CHEM.* (1992), 267:5133–5138). Protein-linked AGEs were measured by competitive ELISA utilizing an AGE standard synthesized by incubation of glucose with BSA. In this ELISA, 1.0 U of AGE activity is defined as the amount of antibody-reactive material that is equivalent to 1.0 µg of AGE-BSA standard. Lipid-derived AGEs were measured in a direct, non-competitive ELISA as follows. For each sample, triplicate 100 µl aliquots of lipid-soluble material (dissolved in methanol) were added to round-bottom, 96 well plates and the solvent evaporated. The wells then were washed three times with PBS/0.05% Tween-20. Antiserum (final dilution 1/1000) was added, the plates were incubated for 1 hour at room temperature, and the wells washed and processed as described for the competitive ELISA. Control samples were developed with pre-immune serum in place of anti-AGE antiserum. Results were quantitated with reference to a standard curve that was obtained by assaying dilutions of AGE-BSA standard that were absorbed to plates in a concentration range from 0.3 ng/ml to 3 µg/ml.

Results

Table 1 shows the formation of AGE-lipids from phosphatidylethanolamine versus the control lipid phosphatidylcholine (in which the amino group is blocked and thus thought to be prevented from reacting with the reducing sugar glucose).

TABLE 1

| Incubation Time | AGE, Units/mg lipid | |
|---|---|---|
| Days | PE + glucose | PC + glucose |
| 0 | <0.005 | <0.005 |
| 10 | 0.024 ± 0.003 | <0.005 |
| 20 | 0.20 ± 0.03 | <0.005 |
| 30 | 0.13 ± 0.02 | <0.005 |
| 40 | 0.15 ± 0.02 | <0.005 |
| 50 | 0.13 ± 0.02 | <0.005 |

EXAMPLE 4

Reaction between aminoguanidine and malonyldialdehyde

Example 2 showed that AGE-lipid formation is accompanied by a parallel increase in lipid oxidation as measured by an increase in the concentration of MDA-like substances. It is notable that this oxidation of lipids occurred without added metals, such as copper, which are commonly employed to initiate lipid oxidation. Additionally, the above examples indicate that aminoguanidine prevents both AGE-lipid formation and lipid oxidation.

To demonstrate that aminoguanidine can react directly with MDA-like aldehydes to prevent their reaction with proteins, aminoguanidine was incubated with MDA.

Methods

Malonyldialdehyde (MDA) standard solutions (0.5 ml) were prepared by dilution of malonaldehyde bis(diethyl acetal) into $H_2O$. Aminoguanidine HCl (0.5 ml) was added, followed by 0.2 ml of the TBA reagent described above. The solution was incubated at room temperature for 10 minutes and TBARS measured by specific fluorescence as described hereinabove.

Results

Figure 8A:
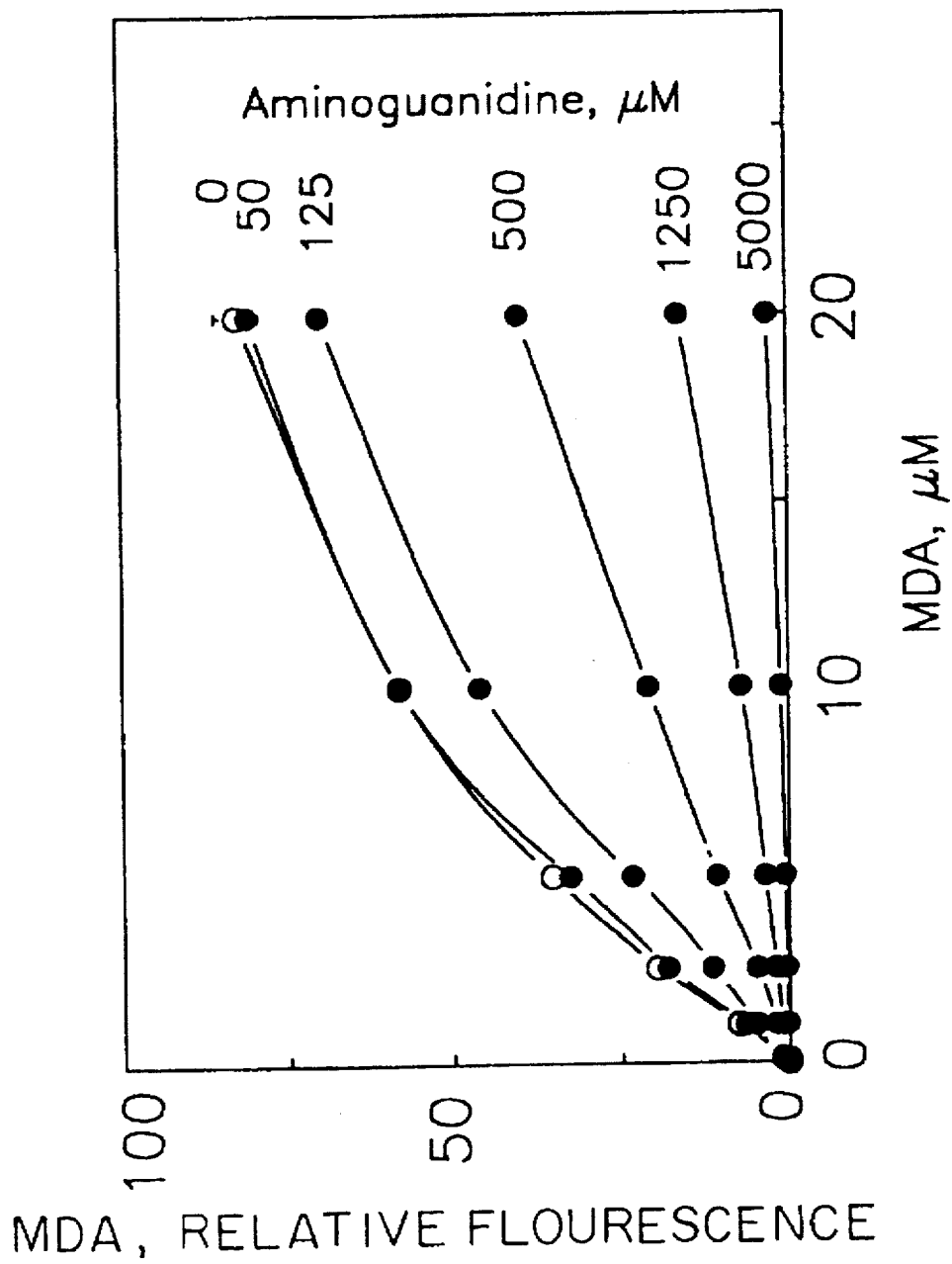
FIG. 8A is a graph showing the concentration-dependent reaction between malonyldialdehyde (bis-[diethylacetal]) (MDA) (0–20 μM) and aminoguanidine (0–500 μm)

The results are shown in FIGS. 8A and B. FIG. 8A shows the progressive inhibition of thiobarbiturate reactivity of MDA (indicated by relative fluorescence) by increasing amounts of aminoguanidine. Thus, aminoguanidine may inhibit protein modification by lipid oxidation products by quenching reactive aldehydes before the latter can participate extensively in subsequent modification of protein amino groups.

FIG. 8B plots one of the latter data sets from FIG. 8A, illustrating the increase in inhibition (A) of the fixed initial amount (10 mM MDA) of thiobarbiturate activity by increasing concentrations of added aminoguanidine.

EXAMPLE 5

To define further the relationship between advanced glycosylation and LDL oxidation in vivo, LDL was isolated from plasma obtained from either non-diabetic or diabetic individuals and analyzed for the presence of lipid-AGEs, apoprotein-AGEs, and oxidative modification. These specimens were obtained from 8 normoglycemic, non-diabetic controls and 16 patients with Type I or Type II diabetes mellitus.

Methods

Plasma LDL (d=1.025–1.063 g/ml) was isolated from healthy, non-hyperglycemic individuals and patients with diabetes mellitus by sequential ultracentrifugation, using 2.7 mM EDTA. The isolated and re-centrifuged LDL was dialyzed extensively against PBS containing 2.7 mM EDTA and 0.2 mM BHT. LDL was sterile filtered before further use and the protein content determined by the Lowry method. The non-diabetic patient group (n=8) had a mean age of 34.6±9.6 years. The diabetic group (n=16) consisted of 5 patients with Type I diabetes and 11 patients with Type II diabetes. The mean age was 55.5±16.3 years and the mean duration of diabetes was 11.9±5.6 years. The mean hemoglobin $A_{1c}$ level was 10.0% ±1.7%. The P values were calculated by the unpaired Student's t-test statistic for comparison between groups.

Results

Figure 9C:
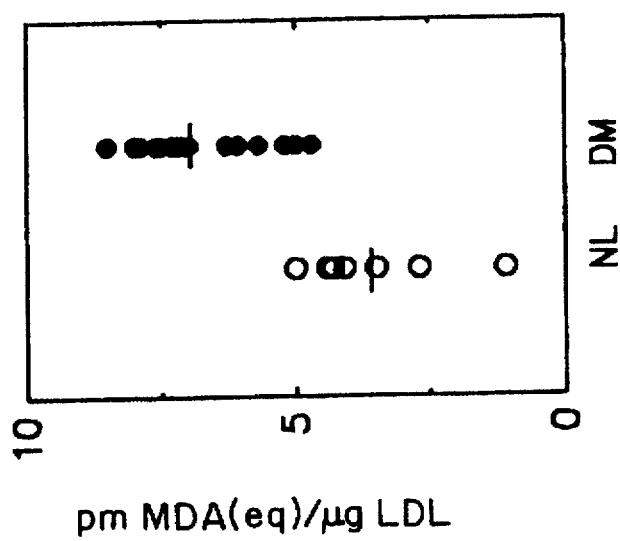
FIGS. 9A–C are graphs of the comparison measurement of AGE and oxidative modification of human LDL isolated from plasma of 8 normoglycemic, non-diabetic individuals (○) and 16 patients with diabetic mellitus.
Figure 9B:
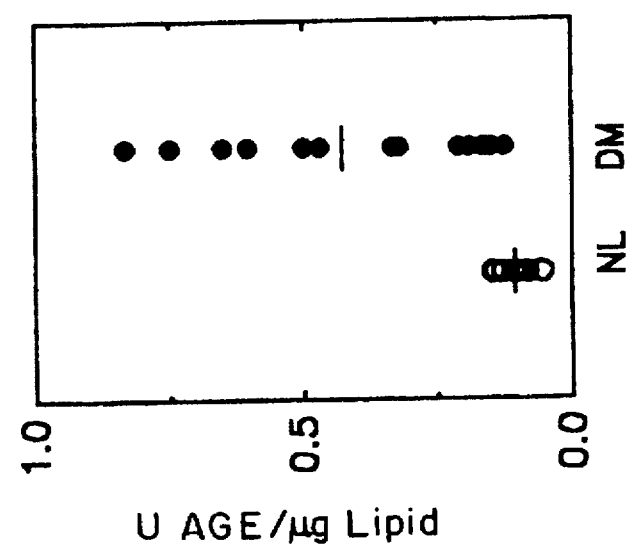
Figure 9A:
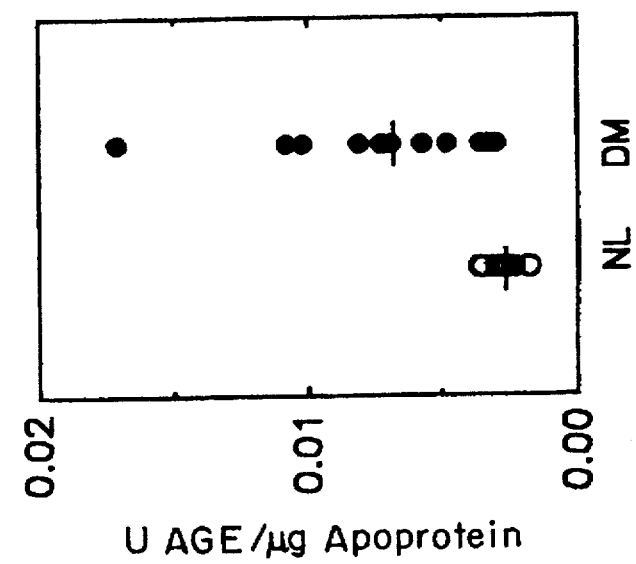

The LDL was analyzed for oxidative modification and then fractionated into lipid and apoprotein components for AGE-ELISA measurements (FIG. 9). In agreement with prior studies, LDL from diabetic individuals was observed to have undergone significantly greater oxidative modification than the LDL from non-diabetic individuals [Normal, Non-diabetics (NL): (n=8) 3.7±1.25 pm MDA equivalents/µg LDL; Diabetics (DM): (n=16) 6.8±1.2 pm MDA equivalents/µg LDL (Mean±SD), P<0.0001)]. Of significance, both the lipid- and the apoprotein-linked AGEs in the diabetic LDL specimens were found to be markedly elevated when compared to the LDL specimens obtained from non-diabetic individuals. Lip±d-AGE levels were elevated almost 4-fold in diabetic patients [Normal, non-diabetic (NL): (n=8) 0.11±0.03 Units of AGE/µg lipid; Diabetics (DM): (n=16) 0.41±0.25 Units of AGE/µg lipid, P<0.005)]. Apoprotein-AGE levels were increased approximately 2-fold in the diabetic samples [NL: (n=8) 0.0028±0.0006 Units of AGE/µg apoprotein; DM: (n=16) 0.0068±0.004 Units of AGE/µg apoprotein, P<0.0001)].

Figure 10A:
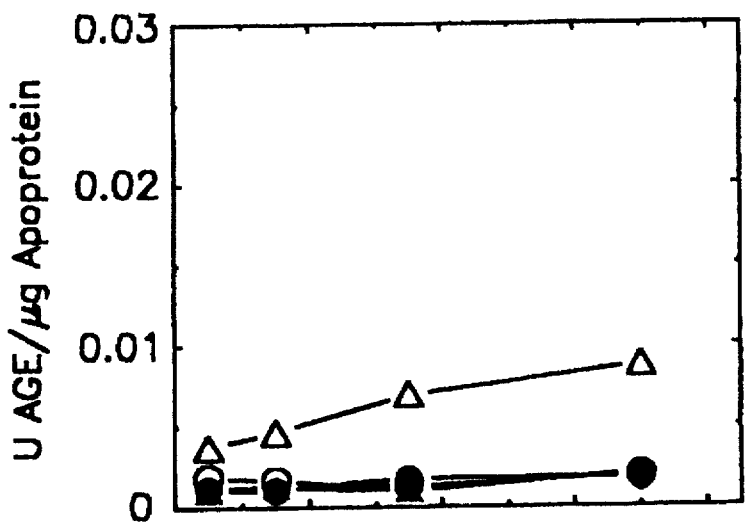
FIGS. 10A–C are graphs of time-dependent reaction of human LDL (2.5 mg/ml) with glucose (200 μmM). At time intervals, samples were dialyzed against PBS/EDTA and portions separated into lipid (FIG. 10B) and apoprotein (FIG. 10A) components for AGE determination or assayed for the presence of ox-LDL (FIG. 10C). LDL incubated with 200 mM glucose (Δ). LDL incubated with 200 mM glucose and 300 mM aminoguanidine (▲). LDL incubated alone (○). LDL incubated with aminoguanidine (●). Values shown are the mean of duplicate determinations.
Figure 10B:
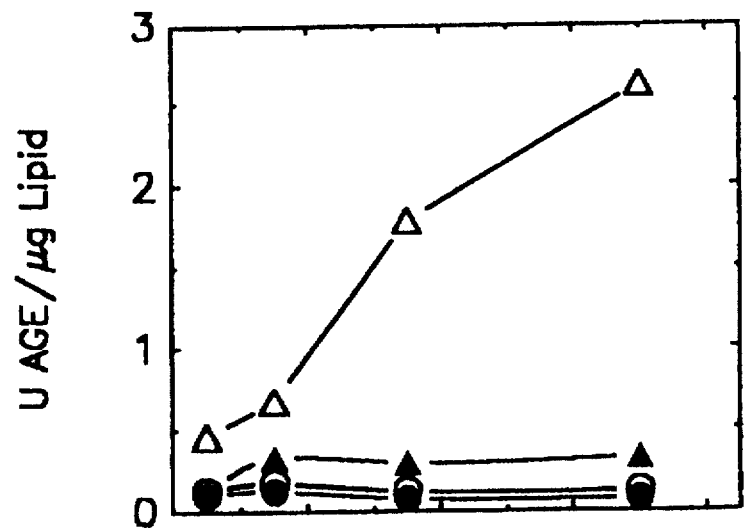
Figure 10C:
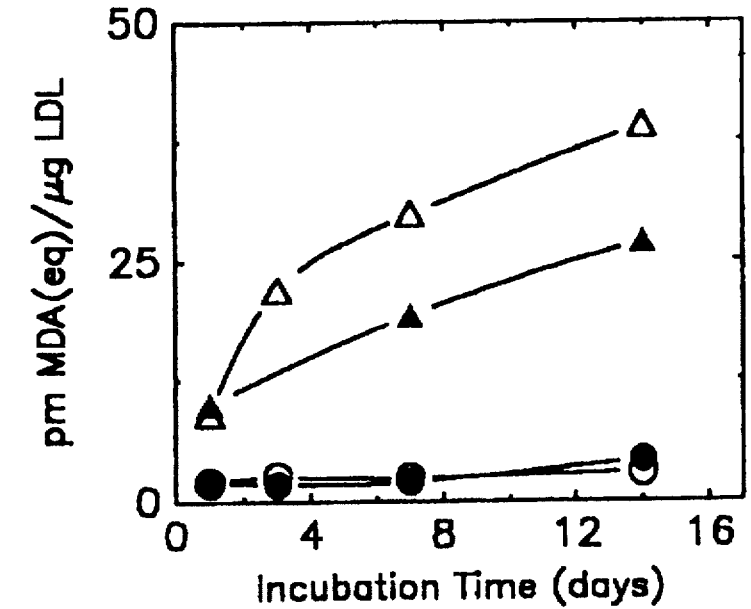

These measurements revealed a similar quantitative ratio between LDL oxidation and the level of AGE-lipid and AGE-apoprotein that was similar to that observed during LDL incubation in vitro (FIG. 10). There also appeared to be a marked increase in the level of lipid-AGEs relative to the level of apoprotein-associated AGEs. Linear regression analysis of these data revealed significant correlation between the level AGE modification and LDL oxidation. For the measurement of AGE-apoprotein versus LDL oxidation, this analysis showed a correlation coefficient of r=0.52 and P<0.01. For AGE-lipid versus LDL oxidation, the corresponding values were r=0.63 and P<0.005.

EXAMPLE 6

It was also postulated that contiguous basic residues (Arg-Lys-Arg) within the receptor-binding domain of apo B might serve as a reactive site for AGE formation, thus preventing normal pathways of LDL clearance. To begin to address this hypothesis, LDL levels were examined in 10 diabetic patients enrolled in a 28-day trial of aminoguanidine (AG), a pharmacological inhibitor of advanced glycosylation.

LDL levels in 10 diabetic patients enrolled in a 28-day trial of aminoguanidine (AG) were measured by the AGE-specific ELISA of Example 3. The efficacy of AG therapy was assessed by reduction in the level of hemoglobin-AGE (Hb-AGE), a circulating marker of advanced glycosylation. The results are given in FIG. 14 and Table 2, below. Table 2 also includes additional data relating to Hb-AGE.

TABLE 2

| Patient Group | Hb-AGE | LDL |
|---|---|---|
| Placebo | 8.9 ± 0.6% reduction | 2.0 ± 0.2% reduction |
| AG treatment | 27.5 ± 1.6% reduction | 29.8 ± 3.1% reduction |
| | Mean ± SD, p < 0.0025 | Mean ± SD, p < 0.002 |

Inhibition of AGE formation was associated with a 30% decrease in LDL levels, as illustrated in FIG. 14.

This study suggests that the advanced glycosylation may account for elevated LDL levels, and that aminoguanidine therapy may serve to improve LDL clearance and diminish the risk of atherogenesis in diabetic patients.

EXAMPLE 7

Figure 11A:
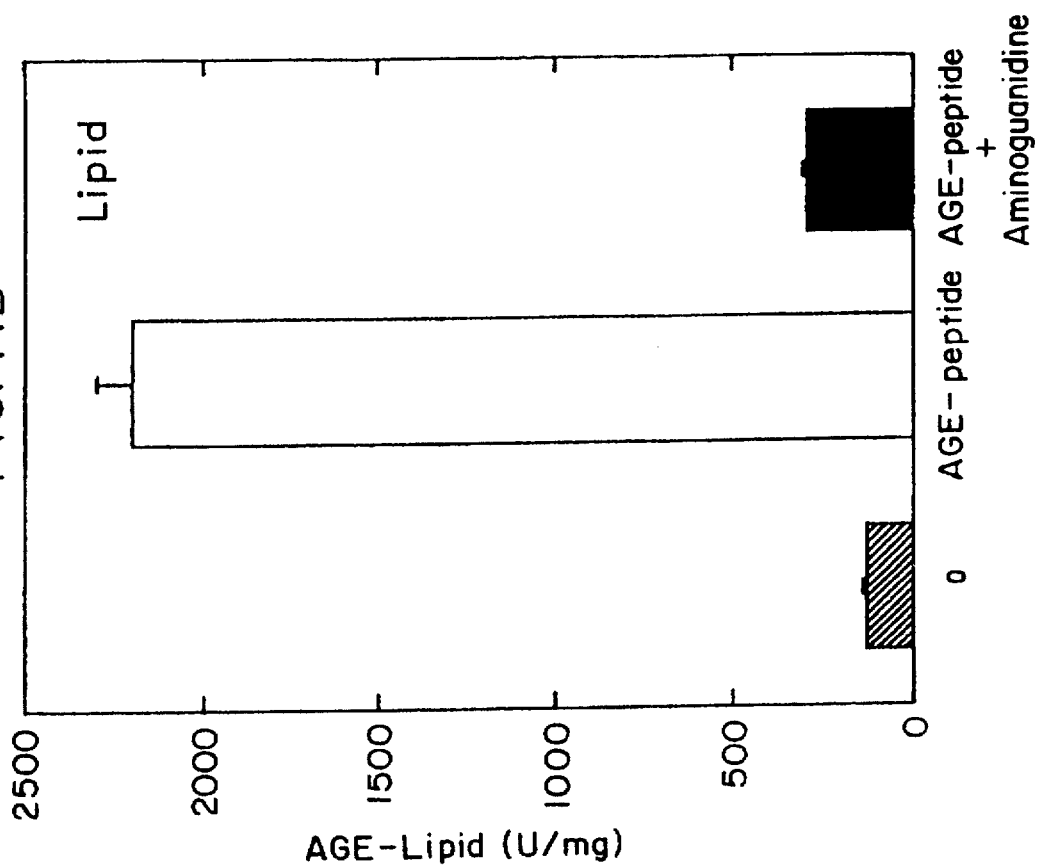
FIG. 11A presents histograms depicting the accumulation of AGEs on apo B that was isolated after incubation of LDL with AGE-peptides, with or without co-incubation with aminoguanidine, as detected in an AGE-specific ELISA.
Figure 11B:
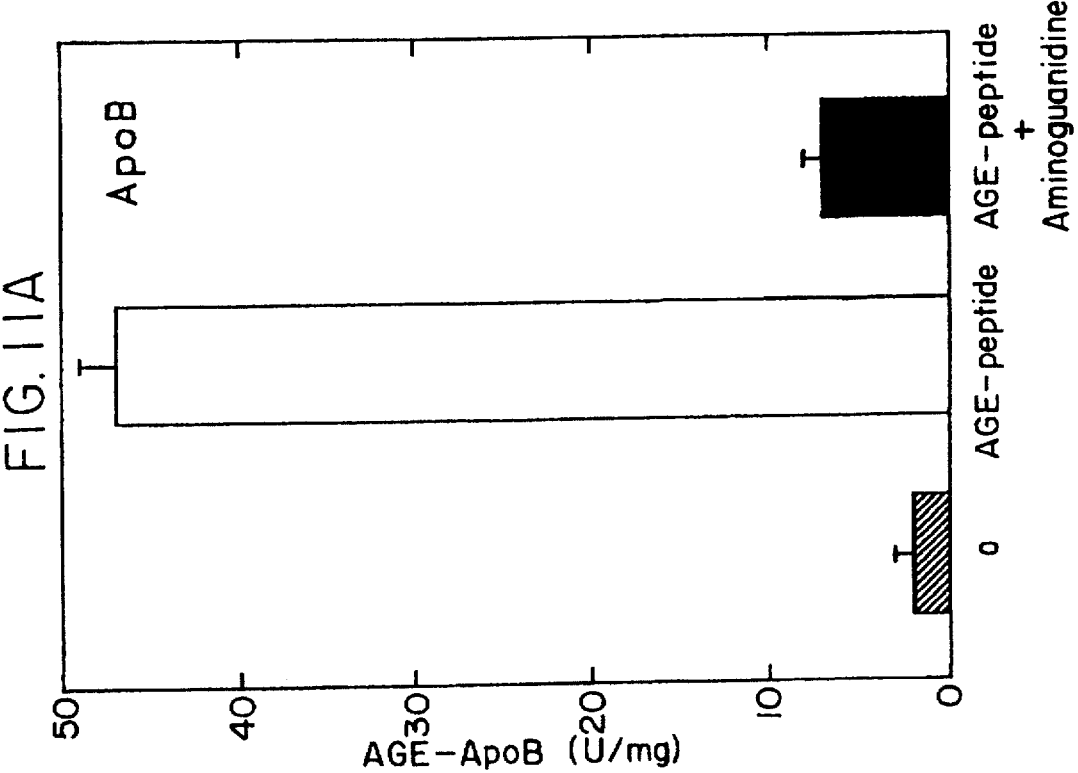
FIG. 11B presents histograms depicting the accumulation of AGEs in a lipid fraction that was isolated after incubation of LDL with AGE-peptides, with or without co-incubation with aminoguanidine, as detected in an AGE-specific ELISA.

To determine whether human AGE-peptides can react with plasma lipoproteins, AGE-peptides isolated from diabetic sera were incubated with human LDL, in the presence or absence of the AGE-inhibitor aminoguanidine (300 mM) for 14 days and the results compared to controls (LDL only) and a parallel incubation of LDL with glucose. AGE levels in apo B and in lipid fractions of LDL were measured by the AGE-specific ELISA procedure of Example 3, and the results given below in Table 3, and in FIG. 11A and 11B. In addition, LDL oxidation was measured as in Example 4, and the AGE-formation was found to parallel LDL-oxidation.

As shown in Table 3 below, marked increases in AGE content of apo B, and of lipid fraction of LDL were noted as a function of time compared to control samples. These values far exceeded those obtained using glucose. AGE-formation paralleled LDL oxidation. In the presence of the AGE-inhibitor aminoguanidine, AGE-formation, as well as lipid oxidation, was markedly inhibited.

In conclusion, circulating AGE-peptides are an important in vivo source of AGE-lipids, and oxidative modification of plasma LDL, in excess of and independent of glucose. Aminoguanidine may be of therapeutic benefit in diabetics, where elevated AGE-peptide levels and hyperlipidemia may be causally linked to accelerated atherosclerosis.

TABLE 3

| Sample | Age Level | LDL Level | Oxidized |
|---|---|---|---|
| Control (LDL only) | Apo B lipid | 2.0 AGE U/mg 130 AGE U/mg | 3 nmoles MDA/mg |
| Glucose (100 mM) + LDL | Apo B lipid | 7 AGE U/mg 630 AGE U/mg | |
| LDL + AGE-peptides | Apo B lipid | 47 AGE U/mg 2200 AGE U/mg | 56 nmoles MDA/mg |

TABLE 3-continued

| Sample | Age Level | LDL Level | Oxidized |
|---|---|---|---|
| LDL + AGE-peptides + AG | Apo B lipid | 7 AGE U/mg 290 AGE U/mg | 12 nmoles MDA/mg |

EXAMPLE 8

Figure 12C:
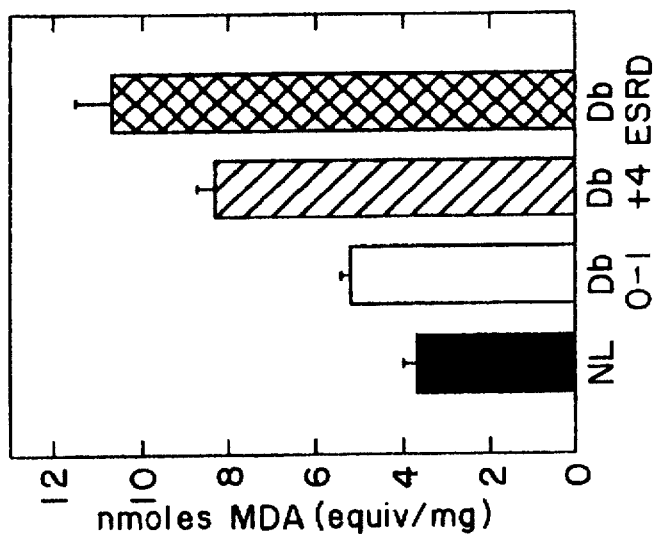
FIG. 12C presents histograms depicting the accumulation of oxidized LDL (detected as MDA equivalents) in plasma LDL that was obtained from human study subjects who were non-diabetic (normal) or diabetic with different numbers of diabetic complications, and diabetic patients with end stage renal disease (ESRD).
Figure 12B:
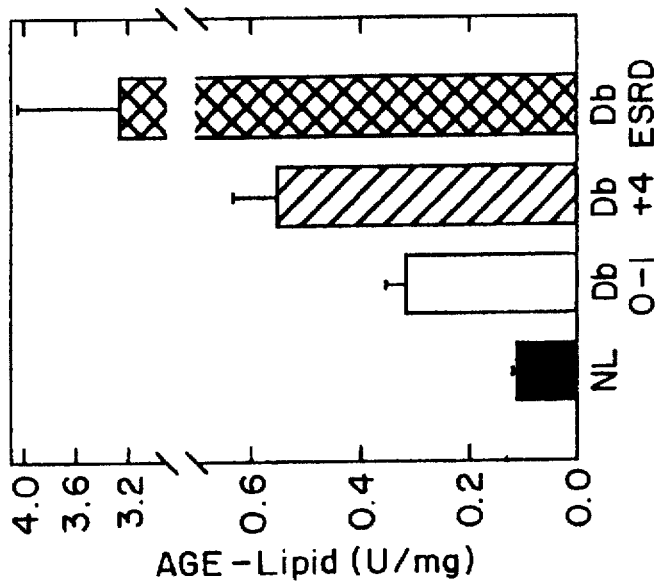
FIG. 12B presents histograms depicting the accumulation of AGEs (as detected in an AGE-specific ELISA) in a lipid fraction that was isolated from LDL obtained from human study subjects who were non-diabetic (normal) or diabetic with different numbers of diabetic complications, and diabetic patients with end stage renal disease (ESRD).
Figure 12A:
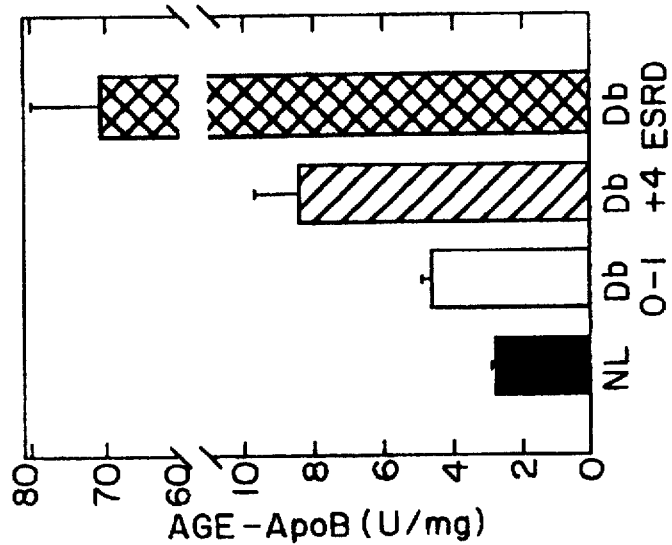
FIG. 12A presents histograms depicting the accumulation of AGEs (as detected in an AGE-specific ELISA) on apo B that was isolated from serum LDL obtained from human study subjects who were non-diabetic (normal) or diabetic with different numbers of diabetic complications, and diabetic patients with end stage renal disease (ESRD).

The AGE-specific ELISA of Example 3 was used to measure AGE moieties attached to the apo B and lipid components of LDL isolated from normal controls (n=17) and diabetic patients (n=43). The results are shown below in Table 4. Additional data reflecting the study of lipid oxidation in these patient samples are presented in FIGS. 12A-12C.

TABLE 4

| Patient Type | AGE level (lipid) | AGE level ApoB |
|---|---|---|
| Control | 109 AGE U/mg | 2.9 AGE U/mg |
| Diabetic patients with none or single complication | 317 AGE U/mg p < 0.005 | 4.6 AGE U/mg p < 0.001 |
| Diabetic patients with multiple complications | 552 AGE U/mg p < 0.001 | 8.4 AGE U/mg p < 0.001 |
| Diabetic patients with severe diabetic nephropathy (ESRD) | 3270 AGE U/mg p < 0.001 | 71 AGE U/mg p < 0.001 |

These data indicate that circulating AGE-LDL levels correlate closely with the number and severity of diabetic complications and support an etiopathological relationship between AGE-modification and both the micro-and macro-vascular complications of diabetes since LDL from diabetic patients with multiple complications contained five-fold higher levels of AGE-lipid and almost three-fold higher levels of AGE-apo B when compared to normal controls. Diabetics with severe diabetic nephropathy (ESRD) showed marked elevation of AGE-modified LDL when compared to diabetic patients without renal involvement.

The results also indicate the AGE-lipid modification was associated with proportionally increased lipid oxidation within each group of patients (non-diabetic: 3.7 nmoles/mg; (0–1 complications): 5.2 nmoles/mg (>4 complications): 8.4 nmoles/mg [measured as nmole MDA equiv/mg LDL].

EXAMPLE 9

An additional patient population was examined to provide data cumulative with the data collected and evaluated in Example 8, above. Accordingly, to determine levels of circulating AGE-low density lipoprotein, apoprotein B, plasma LDL was collected from the selected patients as described in Example 8. Briefly, LDL was delipidated with methanol-ether 1:3 (V/V). Apo B was digested by incubating at 37° C. for 24 hours by using Proteinase K, (1 mg/ml). These samples were inactivated by heating at 70° C. for 1 hour. AGE levels were determined by ELISA as described in Example 3. The results are presented in FIG. 13.

Figure 13:
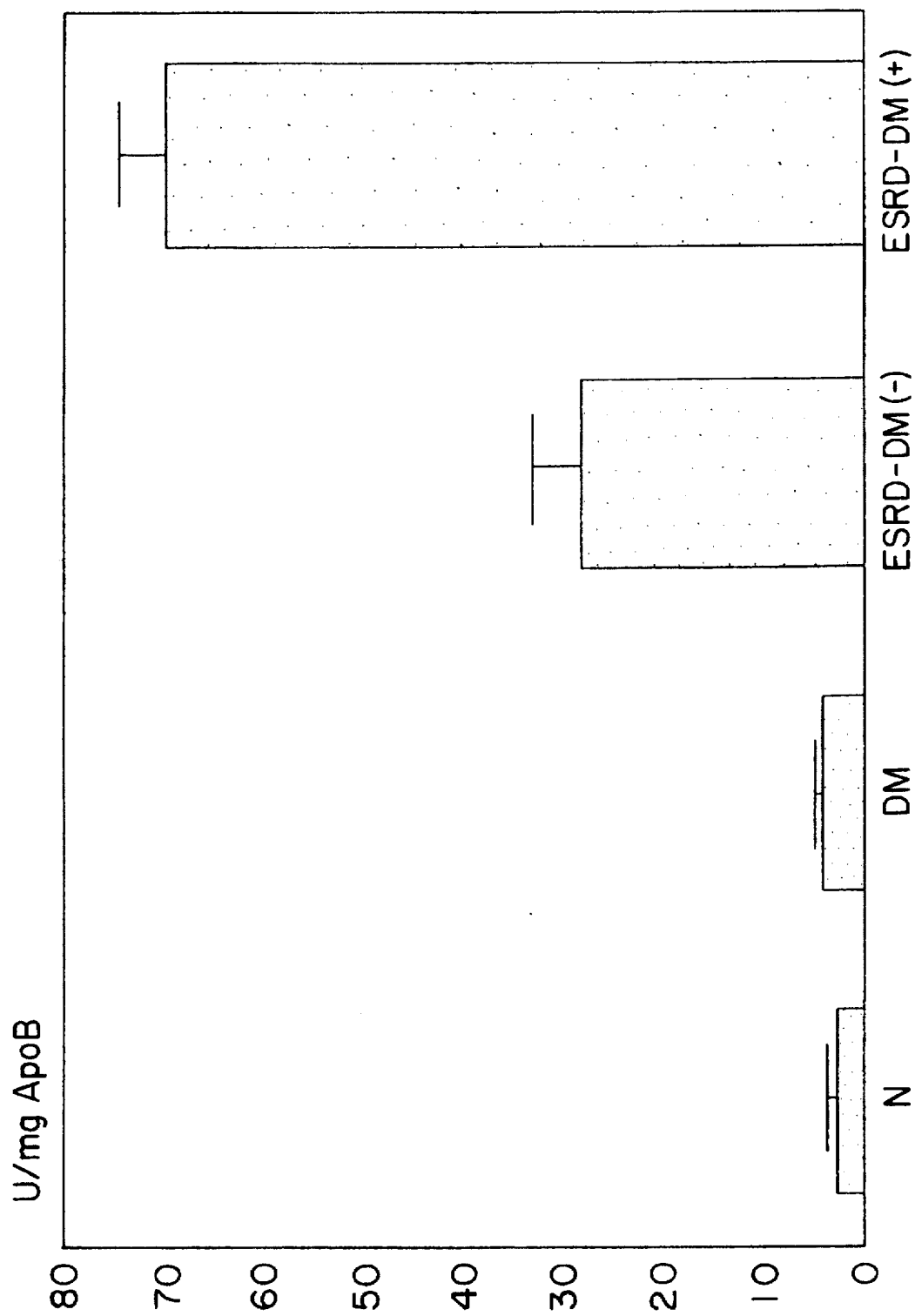
FIG. 13 presents histograms depicting the accumulation of AGEs (as detected in an AGE-specific ELISA) on apo B that was isolated from plasma LDL obtained from human study subjects who were non-diabetic (normal) or diabetic and with or without end stage renal disease.

To obtain a measure of the in vivo "reactivity" of AGE-peptides, AGE levels were determined on a short-lived plasma protein, apoprotein B, in patients with and without diabetes. As shown in FIG. 13, marked elevations of AGE-Apo B were found in LDL from diabetic (mean 69.4±21.7 AGE U/mg, p<0.0001), as well as non-diabetic patients with ESRD (mean 27.6±16.5 AGE U/mg, p<0.0001) compared to normals (2.8±0.5 AGE U/mg), and diabetics with normal renal function (mean 3.9±1.0 AGE U/mg). Since non-diabetics with ESRD are normoglycemic, with normal levels of HbA1c, the data clearly suggest that glucose is not the only source of AGE modification. This is confirmatory of the observation noted in Example 8, above.

DISCUSSION

The data presented here provide an important link between elevated levels of plasma AGEs and accelerated vasculopathy associated with ESRD, consisting of the striking ability of endogenous AGE-peptides to "react" with key proteins, such as collagen and lipoproteins. LDL apoprotein B is a short-lived plasma protein, long implicated in atherogenesis. The efficient generation of AGE-apo B by AGE-peptides in vivo suggested a possible, in vivo marker for the "toxicity" of AGE-peptides. The patient data on circulating AGE-apo B supported this notion.

The level of AGE modification of plasma LDL/Apo B in patients with ESRD was significantly elevated compared to the level of the normal subjects (ten-fold for non-diabetic (ESRD) and twenty-five fold for diabetic (ESRD) patients). Given the relatively short half-life of the LDL particle in blood, the degree of AGE modification in ESRD patients cannot be attributed solely to ambient glucose or other "intermediate" glycosylation products found in plasma. The contribution of these agents in the non-diabetic ESRD patients is also improbable given the normal glucose and HbA1c levels in these non-diabetic patients. Instead, a principal role can be attributed to the so-called "AGE-peptides", or low molecular weight blood-borne AGE-modified species. This is supported by the relatively elevated levels of AGE-peptide in ESRD patients, whether diabetic or not. Further support is for this notion is provided by the relatively modest elevations of AGE-Apo B in diabetic patients with normal renal function, despite their hyperglycemia as reflected in elevated HbA1c.

This interpretation is consistent with the argument that the absence of renal function plays a more important role in total serum AGE accumulation than an increased rate of AGE formation due to hyperglycemia. It is further supported by the findings indicating the clearance of serum AGEs by the kidneys, as measured by urinary excretion, does not differ significantly between normal and diabetics, as long as renal function is preserved.

EXAMPLE 10

When a cerebral vessel is occluded by embolism or thrombus, the extent of the resultant infarction is in part dependent upon the severity of events occurring within the ischemic penumbra, the shell of viable but hypoperfused tissue with potential to survive that surrounds the anoxic and densely infarcted core. Advances in stroke therapy have focused on understanding the pathobiology of cytotoxic factors in the penumbra in order to enhance neuronal survival. Diabetic patients are known to incur more severe strokes than nondiabetics, but the mechanisms of increased neuronal cytotoxicity in diabetic stroke are unknown.

Advanced glycosylation endproducts (AGEs) are reactive, crosslinking, covalent adducts formed by the non-enzymatic reactions of free glucose with protein amino groups in tissues including brain and cerebral vessels. Diabetics have elevated circulating and tissue levels of AGEs which have been implicated in the genesis of diabetic complications. For instance, AGEs have been shown to induce capillary leakage, to increase cytokine production, and to promote procoagulant activity on the endothelial surface. It has recently been reported that exogenously supplied AGEs cause a 9-fold increase in infarct size in a model of focal cerebral ischemia. These data suggest that naturally formed AGEs may play a role in the pathophysiology of increased stroke in diabetics.

In an effort to inhibit the effects of AGEs on brain damage in cerebral ischemia, aminoguanidine, a compound that reacts with glycation adducts to prevent chemical crosslinking, was employed. The results that follow suggest that aminoguanidine significantly mitigates the stroke-enhancing properties of exogenously supplied glycosylation adducts. In addition, aminoguanidine decreases experimentally-induced ischemic infarct volume in the absence of exogenous AGEs, suggesting a potential therapy for stroke and related maladies involving or including ischemia or reperfusion injury, that damage brain, heart, bowel or other organs or tissues, including as examples, peripheral vascular occlusion injury, diabetic retinopathy and damage attendant to angioplasty.

MATERIALS AND METHODS

AGE-albumin was prepared by incubating glucose with bovine serum albumin (Sigma, St. Louis, Mo.) and purifying it by previously established methods. Aminoguanidine was supplied by Regis Chemical Company, Morton Grove, Ill. Male Lewis rats, 270–320 g, were anesthetized with ketamine (120 mg/kg). Through a midline ventral cervical incision, both common carotid arteries were exposed and the right was ligated. In some experiments (where indicated) the tail artery was cannulated to monitor mean arterial pressure and heart rate and provide serial measurements of arterial pH, oxygen, carbon dioxide, and glucose. The right middle cerebral artery was exposed through a 1 mm burr hole drilled approximately 2 mm rostral to the fusion of the zygome with the temporal bone, and elevated 1 mm from the rhinal fissure where it was severed with a cautery. Within 5 minutes of severing the artery, the left common carotid artery was temporarily occluded for 30 minutes or 1 hour (see Table 5, below). Twenty-four hours after experimentally-induced ischemia, brains were removed and coronally sectioned at 1 mm intervals with a brain slicer. Slices were immersed in 2,3,5-triphanyltetrazolium (TTC) (2% in NaCl, 154 mM) for 30 minutes at 37° C. to stain viable tissue. Infarct volume was determined by planimetry on projected images of photographed brain slices, and data expressed as a percentage of total right hemisphere volume infarcted. Statistical analysis on data was performed using a paired T-test.

RESULTS AND DISCUSSION

To examine whether aminoguanidine mitigates against the stroke-enhancing effect of AGEs, we studied the effect of co-administration of AGE-modified albumin (AGE-alb) and aminoguanidine on infarct size, and the effect of aminoguanidine on stroke in the absence of exogenous AGE (see Table 5).

In the first experiment, AGE-alb (235 mg/kg, iv) or albumin (235 mg/kg, iv) was administered 2 hours before severing the right middle cerebral artery. In some animals, aminoguanidine (450 mg/kg, iv) was given with the AGE-alb infusion. As shown in Table 5, aminoguanidine prevented the AGE-alb mediated increase in stroke size as compared to AGE-alb administered alone. These data suggested that aminoguanidine interferes with the cascade of cytotoxic effects elicited by AGEs in the ischemic penumbra.

The next experiment addressed whether aminoguanidine protects against neuronal death, even in the absence of exogenous AGEs. Accordingly, three groups of animals were studied: one received aminoguanidine (160 mg/kg, ip), 30 minutes prior to severing the right middle cerebral artery; another received aminoguanidine (160 mg/kg, ip) 15 minutes after artery severing; and the third group received saline (3 ml/kg, ip) 30 minutes before artery severing. As shown in the table, animals treated with aminoguanidine had significantly decreased infarct size (1.3±0.6%) compared to saline-treated controls (6.0±0.7%, p<0.05). The protective effect of aminoguanidiine was significant even when aminoguanidine was given after severing the artery (1.2±0.4%).

Because a number of physiological responses have been implicated in mediating stroke size after cerebral artery occlusion, we next explored whether aminoguanidine altered blood pressure, heart rate, blood glucose, pH, or oxygen and carbon dioxide tensions at 30 minute intervals before and after stroke. Statistical analysis revealed no significant differences between groups suggesting that aminoguanidine does not exert its effects by altering these physiological parameters. When considered together, these data suggest that the presence of aminoguanidine in the ischemic penumbra may reduce the size of focal cerebral infarction. Likewise, aminoguanidine and its analogs may be used to limit reperfusion injury and other ischemic injury to heart, bowel or other organ or tissue.

"Novel Macrophage Receptor for Glucose-Modified Proteins is Distinct from Previously Described Scavenger Receptors," Vlassara, H., Brownlee, M., and Cerami, A. *J. EXP. MED.* (1986), 164:1301–1309;

"Role of Nonenzymatic Glycosylation in Atherogenesis," Cerami, A., Vlassara, H., and Brownlee, M., *J. CELL. BIOCHEMISTRY* (1986), 30:111–120;

"Characterization of a Solubilized Cell Surface Binding Protein on Macrophages Specific for Proteins Modified Nonenzymatically by Advanced Glycosylation Endproducts,"

Radoff, S., Vlassara, H. and Cerami, A., *ARCH. BIOCHEM. BIOPHYS.* (1988), 263 (2): 418–423;

"Isolation of a Surface Binding Protein Specific for Advanced Glycosylation Endproducts from the Murine Macrophage-Derived Cell Line Raw 264.7", Radoff, S., Vlassara, H., and Cerami, A., *DIABETES*, (1990), 39:1510–1518;

"Two Novel Rat Liver Membrane Proteins that Bind Advanced Glycosylation Endproducts: Relationship to Macrophage Receptor for Glucose-Modified Proteins," Yang, Z., Makita, Z., Horii, Y., Brunelle, S., Cerami, A., Sehajpal, P., Suthanthiran, M. and Vlassara, H., *J. EXP. MED.*, (1991), 174:515–524.

The following listing of publications supplements those set forth above and corresponds by the numbers indicated to like references in the foregoing specification.

1. Witztum, J. L., and D. Steinberg. 1991. Role of oxidized low density lipoprotein in atherogenesis. *J. Clin. Invest.* 88:1785–1792.

TABLE 5

AMINOGUANIDINE ATTENUATES FOCAL STROKE

| EXPERIMENT | GROUP | n | STROKE SIZE (1% HEMISPHERE INFARCTED) | $p < .05$ vs. CONTROLS |
|---|---|---|---|---|
| I (30 min left carotid occlusion) | Control (Albumin) | 6 | .6 + .2% | — |
| | AGE-Albumin | 6 | 5.4 + 2.0% | Yes |
| | AGE-Albumin + Aminoguanidine | 6 | 1.2 + .5% | No |
| II (60 min. left carotid occlusion) | Control (Saline) | 6 | 6.0 + .7% | — |
| | Aminoguanidine (30' pre-sever) | 6 | 1.3 + .6% | Yes |
| | Aminoguanidine (15' post-sever) | 6 | 1.2 + .4% | Yes |

The following publications relate generally to advanced glycosylation endproducts and the reactions in which such products are involved.

"Function of Macrophage Receptor for Nonenzymatically Glycosylated Proteins is Modulated by Insulin Levels," Vlassara, Brownlee and Cerami, *DIABETES* (1986), Vol. 35 Supp. 1, Page 13a;

"Accumulation of Diabetic Rat Peripheral Nerve Myelin by Macrophages Increases with the Presence of Advanced Glycosylation Endproducts," Vlassara, H., Brownlee, M., and Cerami, A. *J. EXP. MED.* (1984), 160:197–207;

"Recognition and Uptake of Human Diabetic Peripheral Nerve Myelin by Macrophages," Vlassara, H., Brownlee, M., and Cerami, A. *DIABETES* (1985), 34(6):553–557;

"High-Affinity-Receptor-Mediated Uptake and Degradation of Glucose-Modified Proteins: A Potential Mechanism for the Removal of Senescent Macromolecules," Vlassara H., Brownlee, M., and Cerami, A., *PROC. NATL. ACAD. SCI. USA* (Sept. 1985), 82:5588–5592;

2. Goldstein, J. L., Y. K. Ho, S. K. Basu, and M. S. Brown. 1979. Binding site on macrophages that mediates uptake and degradation of acetylated low density lipoprotein, producing massive cholesterol deposition. *Proc. Natl. Acad. Sci. USA* 76:333–337.

3. Fogelman, A. M., J. S. Schecter, M. Hokom, J. S. Child, and P. A. Edwards. 1980. Malondialdehyde alteration of low density lipoprotein leads to cholesterol accumulation in human monocyte-macrophages. *Proc. Natl. Acad Sci. USA.* 77:2214–2218.

4. Sparrow, C. P., S. Parthasarathy, and D. Steinberg. 1989. A macrophage receptor that recognizes oxidized LDL but not acetylated LDL. *J. Biol. Chem.* 264:2599–2604.

5. Ross, R. 1986. The pathogenesis of atherosclerosis. An update. *New Eng. J. Med.* 314:488–500.

6. Quinn, M. T., S. Parthasarathy, L. G. Fong, and D. Steinberg. 1987. Oxidatively modified low density lipoprotein: a potential role in recruitment and retention of monocyte/macrophages during atherogenesis. *Proc. Natl. Acad. Sci. USA* 84: 2995–2998.

7. Hessler, J. R., D. W. Morel, L. J. Lewis, and G. M. Chisolm. 1983. Lipoprotein oxidation and lipoprotein-induced cytotoxicity. *Arteriosclerosis* 3: 215–222.

8. Kugiyama, K., S. A. Kerns, J. D. Morrisett, R. Roberts, and P. D. Henry. 1990. Impairment of endothelium-dependent arterial relaxation by lysolecithin in modified low-density lipoproteins. *Nature* 344: 160–162.

9. Rajavashisth, T. B., A. Andalibi, M. C. Territo, J. A. Berliner, M. Navab, A.M. Fogelman, and A. J. Lusis. 1990. Induction of endothelial cell expression of granulocyte and macrophage colony-stimulating factors by modified low-density lipoproteins. *Nature* 344: 254–257.

10. Cushing, S. D., J. A. Berliner, A. J. Valente, M. Navab, F. Parhami, R. Gerrity, C. J. Schwartz, and A. M. Fogelman. 1990. Minimally modified low density lipoprotein induces monocyte chemotactic protein 1 in human endothelial cells and smooth muscle cells. *Proc. Natl. Acad. Sci. USA.* 87: 5134–5138.

11. Kita, T., Y. Nagano, M. Yokode, K. Ishii, N. Kume, A. Ooshima, H. Yoshida, and C. Kawai. 1987. Probucol prevents the progression of atherosclerosis in Watanabe heritable hyperlipidemic rabbit, an animal model for familial hypercholesterolemia. *Proc. Natl. Acad. Sci. USA* 84:5928–5931.

12. Esterbauer, H. G. Jurgens, O. Quehenberger, and Koller, E. 1987. Autoxidation of human low density lipoprotein: loss of polyunsaturated fatty acids and vitamin E and generation of aldehydes. *J. Lipid Res.* 28: 505–509.

13. Quehenberger, O., E. Koller, G. Jurgens, and H. Esterbauer. 1987. Investigation of lipid peroxidation in human low density lipoprotein. *Free Radical Res. Commun.* 3: 233–242.

14. Steinbrecher, U. P. 1987. Oxidation of human low density lipoprotein results in derivitization of lysine residues of apolipoprotein B by lipid peroxide decomposition products. *J. Biol. Chem.* 262:3603–3608.

15. Steinbrecher, U. P., S. Parthasarathy, D. S. Leake, J. L. Witztum, and D. Steinberg. 1984. Modification of low density lipoprotein by endothelial cells involves lipid peroxidation and degradation of low density lipoprotein phospholipids. *Proc. Natl. Acad. Sci. USA* 81: 3883–3887.

16. Parthasarathy, S., E. Wieland, and D. Steinberg. 1989. A role for endothelial cell lipoxygenase in the oxidative modification of low density lipoprotein. *Proc. Natl. Acad. Sci. USA* 86:1046–1050.

17. Klaassen, C. D. 1985. Heavy metals and heavy metal antagonists, In Goodman and Gilman's The Pharmacological Basis of Therapeutics. A. G. Gilman, L. S. Goodman. T. W. Rall, and F. Murad. Macmillan, New York. 1605–1627.

18. Frei, B., Y. Yamamoto, D. Niclas, and B. N. Ames. 1988. Evaluation of an isoluminol chemiluminescence assay for the detection of hydroperoxides in human blood plasma. *Anal. Biochem.* 175:120–130.

19. Frei, B., R. Stocker, and B. N. Ames. 1988. Antioxidant defenses and lipid peroxidation in human blood plasma. *Proc. Natl. Acad. Sci. USA* 85:9748–9752.

20. Bucala, R., and A. Cerami. 1992. Advanced glycosylation: chemistry, biology, and implications for diabetes and aging. *Adv. Pharmacol.* 23:1–34.

21. Njoroge, F. G., and V. M. Monnier. 1989. The chemistry of the Maillard reaction under physiological conditions: A review. *Prog. Clin. Biol. Res.* 304:85–107.

22. Brownlee, M., A. Cerami, and H. Vlassara. 1988. Advanced glycosylation endproducts in tissue and the biochemical basis of diabetic complications. *N. Eng. J. Med.* 318:1315–1321.

23. Monnier, V. M., R. R. Kohn, and A. Cerami. 1984. Accelerated age-related browning of human collagen in diabetes mellitus. *Proc. Natl. Acad. Sci. USA.* 81:583–587.

24. Bucala, R., K. J. Tracey, and A. Cerami. 1991. Advanced glycosylation products quench nitric oxide and mediate defective endothelium-dependent vasodilatation in experimental diabetes. *J. Clin. Invest.* 87:432–438.

25. Vlassara, H., M. Brownlee, and A. Cerami. 1985. High-affinity-receptor-mediated uptake and degradation of glucose-modified proteins: A potential mechanism for the removal of senescent macromolecules. *Proc. Natl. Acad. Sci USA* 82:5588–5592.

26. Esposito, C., H. Gerlach, J. Brett, D. Stern, and H. Vlassara. 1989. Endothelial receptor-mediated binding of glucose-modified albumin is associated with increased monolayer permeability and modulation of cell surface coagulant properties. *J. Exp. Med.* 170:1387–1407.

27. Vlassara, H., M. Brownlee, K. R. Manogue, C. A. Dinarello, and A. Pasagian. 1988. Cachectin/TNF and IL-1 induced by glucose-modified proteins: Role in normal tissue remodelling. *Science* 240:1546–1548.

28. Jain, S. K., R. McVie, J. Duett, and J. J. Herbst. 1989. Erythrocyte membrane lipid peroxidation and glycosylated hemoglobin in diabetes. *Diabetes* 38:1539–1543.

29. Nishigaki, I., M. Hagihara, H. Tsunekawa, M. Maseki, and K. Yagi. 1981. Lipid peroxide levels of serum lipoprotein fractions of diabetic patients. *Biochem. Med.* 25:373–378.

30. Armstrong, D. N. Abdella, A. Salman, N. Miller, E. A. Rahman, and M. Bojancyzk. 1992. Relationship of lipid peroxides to diabetic complications. *J. Diabetes Complications* 6:116–122.

31. London, E., and G. W. Feigenson. 1978. A convenient and sensitive fluorescence assay for phospholipid vesicles using diphenylhexatriene. *Anal. Biochem.* 88:203–211.

32. Jain, S. K., and D. Subrahmanyan. 1978. Two dimensional thin-layer chromatography of polar lipids. *Ital. J. Biochem.* 27:11–18.

33. Havel, R. J., H. A. Eder, and J. H. Bragdon. 1955. Distribution and chemical composition of ultracentrifugally separated lipoproteins in human serum. *J. Clin. Invest.* 34:1345–1353.

34. Lowry, O., N. J. Rosebrough, A. L. Farr, and R. J. Randall. 1951. Protein measurement with Folin phenol reagent. *J. Biol. Chem.* 193: 265–275.

35. Makita, Z., H. Vlassara, A. Cerami, and R. Bucala. 1992. Immunochemical detection of advanced glycosylation end products in vivo. *J. Biol. Chem.* 267: 5133–5138.

36. Makita, Z., H. Vlassara, E. Rayfield, K. Cartwright, E. Friedman, R. Rodby, A. Cerami, and R. Bucala. 1992. Hemoglobin-AGE: A circulating marker of advanced glycosylation. *Science* 258:651–653.

37. Kikugawa, K., T. Kojima, S. Yamaki, and H. Kosugi. 1992. Interpretation of the thiobarbituric acid reactivity of rat liver and brain homogenates in the presence of ferric ion and ethylenediaminetetraacetic acid. *Anal. Biochem.* 202:249–255.

38. Ohkawa, H., N. Ohishi, and K. Yagi. 1979. Assay for lipid peroxides in animal tissues by thiobarbituric acid reaction. *Anal. Biochem.* 95:351–358.

39. Chen, H. -J. C., and A. Cerami. 1992. Mechanism of inhibition of advanced glycosylation by aminoguanidine in vitro. *J. Carbohydrate Chem.* (in press).

40. Picard, S., S. Parthasarathy, J. Fruebis, and J. L. Witztum. 1992. Aminoguanidine inhibits oxidative modification of low density lipoprotein and the subsequent increase in uptake by macrophage scavenger receptors. *Proc. Natl. Acad. Sci. USA* 89:6876–6880.

41. Hicks, M., L. Delbridge, D. K. Yue, and T. S. Reeve. 1988. Catalysis of lipid peroxidation by glucose and glycosylated collagen. *Biochem. Biophys. Res. Commun.* 151:649–655.

42. Mullarkey, C. J., D. Edelstein, and M. Brownlee. 1990. Free radical generation by early glycation products: A mechanism for accelerated atherogenesis in diabetes. *Biochem. Biophys. Res. Commun.* 173:932–939.

43. Pongor, S., P. C. Ulrich, F. A. Bencsath, and A. Cerami. 1984. Aging of proteins: isolation and identification of a fluorescent chromophore from the reaction of polypeptides with glucose. *Proc. Natl. Acad. Sci. USA*, 81:2684–2688.

44. Ahmed, M. U., J. A. Dunn, M. D. Walla, S. R. Thorpe, and J. W. Baynes. 1988. Oxidative degradation of glucose adducts to protein. *J. Biol. Chem.* 263:8816–8821.

45. Grandhee, S. K., and V. M. Monnier. 1991. Mechanism of formation of the Maillard protein cross-link pentosidine. Glucose, fructose, and ascorbate as pentosidine precursors. *J. Biol. Chem.* 266:11649–11653.

46. Namiki, M., and T. Hayashi. 1981. Formation of novel free radical products in an early stage of Maillard reaction. *Prog. Fd. Nutr. Sci.* 5:81–91.

47. Tsuchida, M., T. Miura, and K. Aibara. 1987. Lipofuscin and lipofuscin-like substances. *Chem. Phys. Lipids.* 44:297–325.

48. T. Soulis-Liparota, M. Cooper, D. Papazoglou, B. Clarke, and G. Jerums. 1991. Retardation by aminoguanidine of development of albuminuria, mesangial expansion, and tissue fluorescence in streptozotocin-induced diabetic rat. *Diabetes* 40:1328–1334.

49. Hammes, H. P., S. Martin, K. Federlin, K. Geisen, and M. Brownlee. 1991. Aminoguanidine treatment inhibits the development of experimental diabetic retinopathy. *Proc. Natl. Acad. Sci. USA* 88:11555–11558.

50. Yagihashi, S., M. Kamijo, M. Baba, N. Yagihashi, and K. Nagai, 1992. Effect of aminoguanidine on functional and structural abnormalities in peripheral nerve of STZ-induced diabetic rats. *Diabetes* 41:47–52.

51. O'Brien, R. C., S. Panagiotopoulos, M. E. Cooper, and G. Jerums. 1992. Anti-atherogenic effect of aminoguanidine, an inhibitor of advanced glycation. *Diabetes* 41, (Suppl. 1) 16A.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method for estimating the course and extent of in vivo lipid oxidation in a mammal comprising measuring the presence and amount of AGE-lipids in said mammal.

2. The method of claim 1, wherein said AGE-lipids are measured by an in vitro procedure.

3. The method of claim 1, comprising the steps of:
   A. preparing at least one biological sample taken from said mammal in which said AGE-lipids are suspected to be present;
   B. immobilizing the biological sample of Step A or a binding partner to AGE-lipid or AGE-lipid related material, on a suitable substrate, and labelling the other of the materials not immobilized;
   C. incubating said sample with said binding partner for a period of time sufficient for said binding partner to become bound to any AGE-lipid or AGE-bearing lipid-related material present in said sample;
   D. removing any unbound material from Step C, and
   E. comparing the amount of label bound to said sample to a standard.

4. The method of claim 3, wherein said binding partner is selected from the group consisting of a receptor for an AGE, and an antibody reactive with or capable of binding to said AGE-lipid.

5. The method of claim 4, wherein said antibody to said AGE-lipid is selected from the group consisting of polyclonal antibodies, monoclonal antibodies, and chimeric antibodies.

6. The method of claim 1 comprising a method for monitoring the level of low density lipoprotein in said mammal.

7. The method of claim 1, comprising a method for diagnosing the likelihood or onset, and/or for monitoring the course and severity of a pathology selected from atherosclerosis, vascular disease, diabetes, diabetic nephropathy, and hypercholesterolemia.

8. A method of testing the ability of a drug or other entity to prevent blockade of the LDL receptor binding domain on apo B, which comprises disposing a quantity of apo B with unbound LDL receptor binding domain in a suitable medium, simultaneously adding a quantity of an material capable of forming an AGE on said binding domain, and the drug under test, and thereafter measuring the quantity of AGE-apo B, if any, that is formed.

* * * * *

UNITED STATES PATENT AND TRADEMARK OFFICE
CERTIFICATE OF CORRECTION

PATENT NO. : 5,700,447
DATED : December 23, 1997
INVENTOR(S) : Richard J. Bucala et al It is certified that error appears in the above-indentified patent and that said Letters Patent is hereby corrected as shown below:

On the title page, item [73],

Under the heading "Assignee"
delete "Picowder" and insert

--Picower--

Signed and Sealed this

Thirty-first Day of March, 1998

Attest:

BRUCE LEHMAN

Attesting Officer        Commissioner of Patents and Trademarks